(12) United States Patent
Hoendervoogt et al.

(10) Patent No.: US 8,192,398 B2
(45) Date of Patent: Jun. 5, 2012

(54) MEDICAL DEVICE AND MEDICAL INSTRUMENT ALIGNMENT

(75) Inventors: Jason J. Hoendervoogt, Scottsdale, AZ (US); Timothy J. Denison, Minneapolis, MN (US); Todd A. Kallmyer, Tempe, AZ (US); Scott L. Kalpin, Harris, MN (US); Scott A. Sarkinen, Greenfield, MN (US)

(73) Assignee: Medtronic, Inc., Minneapolis, MN (US)

( * ) Notice: Subject to any disclaimer, the term of this patent is extended or adjusted under 35 U.S.C. 154(b) by 1119 days.

(21) Appl. No.: 12/047,779

(22) Filed: Mar. 13, 2008

(65) Prior Publication Data

US 2009/0234302 A1 Sep. 17, 2009

(51) Int. Cl.
*A61M 5/00* (2006.01)

(52) U.S. Cl. ............... 604/116; 604/891.1; 604/288.01; 600/424

(58) Field of Classification Search .................. 604/513, 604/116, 117, 288.01, 288.02, 288.03, 288.04, 604/891.1; 600/424
See application file for complete search history.

(56) References Cited

U.S. PATENT DOCUMENTS

| | | | |
|---|---|---|---|
| 4,222,374 A | 9/1980 | Sampson et al. | |
| 4,573,994 A | 3/1986 | Fischell et al. | |
| 4,784,646 A | 11/1988 | Feingold | |
| 4,804,054 A | 2/1989 | Howson et al. | |
| 5,171,228 A | 12/1992 | McDonald | |
| 5,571,083 A * | 11/1996 | Lemelson | ...................... 604/522 |
| 5,758,667 A | 6/1998 | Slettenmark | |
| 5,944,023 A | 8/1999 | Johnson et al. | |
| 6,044,297 A | 3/2000 | Sheldon et al. | |
| 6,293,922 B1 | 9/2001 | Haase | |
| 6,305,381 B1 | 10/2001 | Weijand et al. | |
| 6,466,821 B1 | 10/2002 | Pianca et al. | |
| 7,044,932 B2 | 5/2006 | Borchard et al. | |
| 7,191,011 B2 | 3/2007 | Cantlon | |
| 7,806,122 B2 | 10/2010 | Hoendervoogt et al. | |
| 2005/0137578 A1 | 6/2005 | Heruth et al. | |
| 2007/0129774 A1 | 6/2007 | Bourget et al. | |
| 2007/0213837 A1 * | 9/2007 | Ferreri et al. | ............. 623/23.65 |
| 2008/0013053 A1 | 1/2008 | Anson | |

FOREIGN PATENT DOCUMENTS

| | | |
|---|---|---|
| EP | 1 832 254 A1 | 9/2007 |
| WO | WO 2005/089860 | 9/2005 |
| WO | WO 2008/140901 | 11/2008 |

OTHER PUBLICATIONS

Notification of Transmittal of the International Search Report and the Written Opinion of the International Searching Authority, or the Declaration for corresponding PCT Application No. PCT/US2008/086076 dated Apr. 16, 2009 (12 pgs.).

* cited by examiner

*Primary Examiner* — Bhisma Mehta

(74) *Attorney, Agent, or Firm* — Scott A. Marks; Shumaker & Siefert P.A.

(57) ABSTRACT

Systems and methods for orienting a medical instrument relative to at least a portion of a medical device include a first tilt detector associated with the medical instrument and a second tilt detector associated with the medical device. The first tilt detector may be within an orientation device that is coupled to or separate from the medical instrument. The tilt detectors generate signals that may be used to determine the relative orientation between at least a portion of the medical device and medical instrument. For example, in some embodiments, the signals may be used to determine whether the orientations of the portion of the medical device and the medical instrument substantially match.

20 Claims, 15 Drawing Sheets

MEDICAL DEVICE AND MEDICAL INSTRUMENT ALIGNMENT

TECHNICAL FIELD

The invention relates to medical devices, and, more particularly, the alignment of medical devices and medical instruments.

BACKGROUND

Some implantable medical devices, such as implantable drug pumps, include fluid reservoirs that may be accessed through ports, which may be self-sealing. The medical device may be configured to deliver a therapeutic agent from the fluid reservoir to a patient according to a therapy program, which may, for example, specify the size of a bolus delivered to the patient, the concentration of the therapeutic agent, and/or the delivery rate of the therapeutic agent. After the medical device is implanted within a patient, it may be desirable to percutaneously access the reservoir of the implanted medical device in order to refill the reservoir with a therapeutic agent, flush out the reservoir or change the fluid in the reservoir.

SUMMARY

In general, the invention is directed toward systems and methods for orienting a medical instrument relative to at least a portion of a medical device. In some cases, the medical device may be implanted within a patient and the medical instrument may be external to the patient. For example, the medical device may be a therapeutic agent delivery device, such as a drug pump, and the medical instrument may be a needle used to refill a reservoir of the therapeutic agent delivery device.

As described herein, an alignment system may include a first tilt detector (e.g., an accelerometer) associated with a medical device, where the first tilt detector provides information indicative of an orientation of the medical device. The first tilt detector may be in a known orientation relative to at least a portion of the medical device. Information from the first tilt detector may be used to determine an orientation of the portion of the medical device relative to a reference point, and may be used to orient a medical instrument relative to the portion of the medical device. For example, the information from the first tilt detector may be used to determine a direction in which the portion of the medical device is facing relative to a reference point.

In some embodiments, the reference point may be a baseline orientation of the portion of the medical device or an orientation of a second tilt detector that is associated with the medical instrument. For example, the second tilt detector may be incorporated in an orientation device that is coupled to a medical instrument or separate from the medical instrument. In embodiments including a second tilt detector associated with a medical instrument, the relative orientation between the medical device and medical instrument may be determined based on signals from the respective tilt detectors.

In some embodiments, an orientation device may include an indicator that provides information to a user based on signals from the first and second tilt detectors. The information may be indicative of a relative orientation between the orientation device and the portion of the implantable medical device. For example, the information may indicate whether a first signal from the first tilt detector substantially matches a second signal from a second tilt detector. As another example, the information may include instructions to guide a user to position an orientation device or a medical instrument relative to the portion of the implantable medical device. As another example, the information may include a determined offset between the signals, which may indicate the tilt of orientation device relative to the implantable medical device.

In embodiments including an orientation device comprising a tilt detector, a clinician may utilize the orientation device to align an orientation of a medical instrument with an orientation of at least a portion of a medical device. For example, the clinician may utilize the orientation device to align a needle with a reservoir port opening of an implanted drug pump. The orientation device may include a display or another indicator that indicates when an orientation of the orientation device substantially matches the orientation of the port opening, or the indicator may provide instructions that guide the clinician to position the orientation device such that its orientation substantially matches an orientation of the port opening of the implanted drug pump.

In one embodiment, the invention is directed to a system comprising an implantable medical device comprising a first tilt detector in a known orientation relative to at least a portion of the implantable medical device, an orientation device comprising a second tilt detector, and an indicator that provides information to a user based on signals from the first and second tilt detectors. The information is indicative of a relative orientation between the orientation device and the portion of the implantable medical device.

In another embodiment, the invention is directed to a system comprising an implantable medical device comprising a first accelerometer in a known orientation relative to at least a portion of the implantable medical device, a medical instrument, and a second accelerometer in a known orientation relative to the medical instrument. The first accelerometer generates a first signal indicative of a first orientation of at least the portion of the implantable medical device. The second accelerometer generates a second signal indicative of a second orientation of the second accelerometer In another embodiment, the invention is directed to a device comprising a first tilt detector, an indicator, a receiver that receives signals from a second tilt detector associated with an implantable medical device, and a processor that controls the indicator to provide information to a user based on signals from the first and second tilt detectors. The information is indicative of a relative orientation between the orientation device and the implantable medical device.

In another embodiment, the invention is directed to a method comprising receiving a first signal from a first tilt detector associated with an implantable medical device, receiving a second signal, and providing information to a user indicative of a relative orientation between at least a portion of the implantable medical device and an orientation device based on the first and second signals. The second signal may be, for example, generated by a second tilt detector associated with an orientation device or may be a signal indicative of a baseline orientation of at least a portion of the implantable medical device.

In another embodiment, the invention is directed to a method comprising receiving a first signal from a first tilt detector associated with an implantable medical device, and determining an offset between the first signal and a second signal to determine a relative orientation between the implantable medical device and an orientation device.

In another embodiment, the invention is directed to a method comprising placing an external device in a first position relative to an implantable medical device, where the implantable medical device comprises a first tilt detector and the external device is associated with a second tilt detector, receiving information indicative of a relative orientation between the implantable medical device and the external device, where the information is based on a first signal from the first tilt detector and a second signal from the second tilt detector, and adjusting the position of the external device based on the first and second signals. The external device may be, for example, an orientation device or a medical instrument, which may be coupled to an orientation device.

In another embodiment, the invention is directed to a system comprising means for receiving a first signal from a first tilt detector associated with an implantable medical device, means for receiving a second signal from a second tilt detector associated with an orientation device, and means for providing information to a user indicative of a relative orientation between at least a portion of the implantable medical device and the orientation device.

The details of one or more embodiments of the invention are set forth in the accompanying drawings and the description below. Other features, objects, and advantages of the invention will be apparent from the description and drawings, and from the claims.

DETAILED DESCRIPTION

Medical devices are useful for treating, managing or otherwise controlling various patient conditions or disorders, such as, but not limited to, pain (e.g., chronic pain, postoperative pain or peripheral and localized pain), tremor, movement disorders (e.g., Parkinson's disease), diabetes, epilepsy, neuralgia, chronic migraines, urinary or fecal incontinence, sexual dysfunction, obesity, gastroparesis, mood disorders or other neurological disorders. Some medical devices may be configured to deliver one or more therapeutic agents, alone or in combination with other therapies, such as electrical stimulation, to one or more target tissue sites within a patient. For example, in some cases, a medical device may deliver insulin to a patient with diabetes. Depending upon the type of therapy delivered by the medical device, the medical device may be implanted in the patient for chronic therapy delivery (e.g., longer than a temporary, trial basis).

Figure 1:
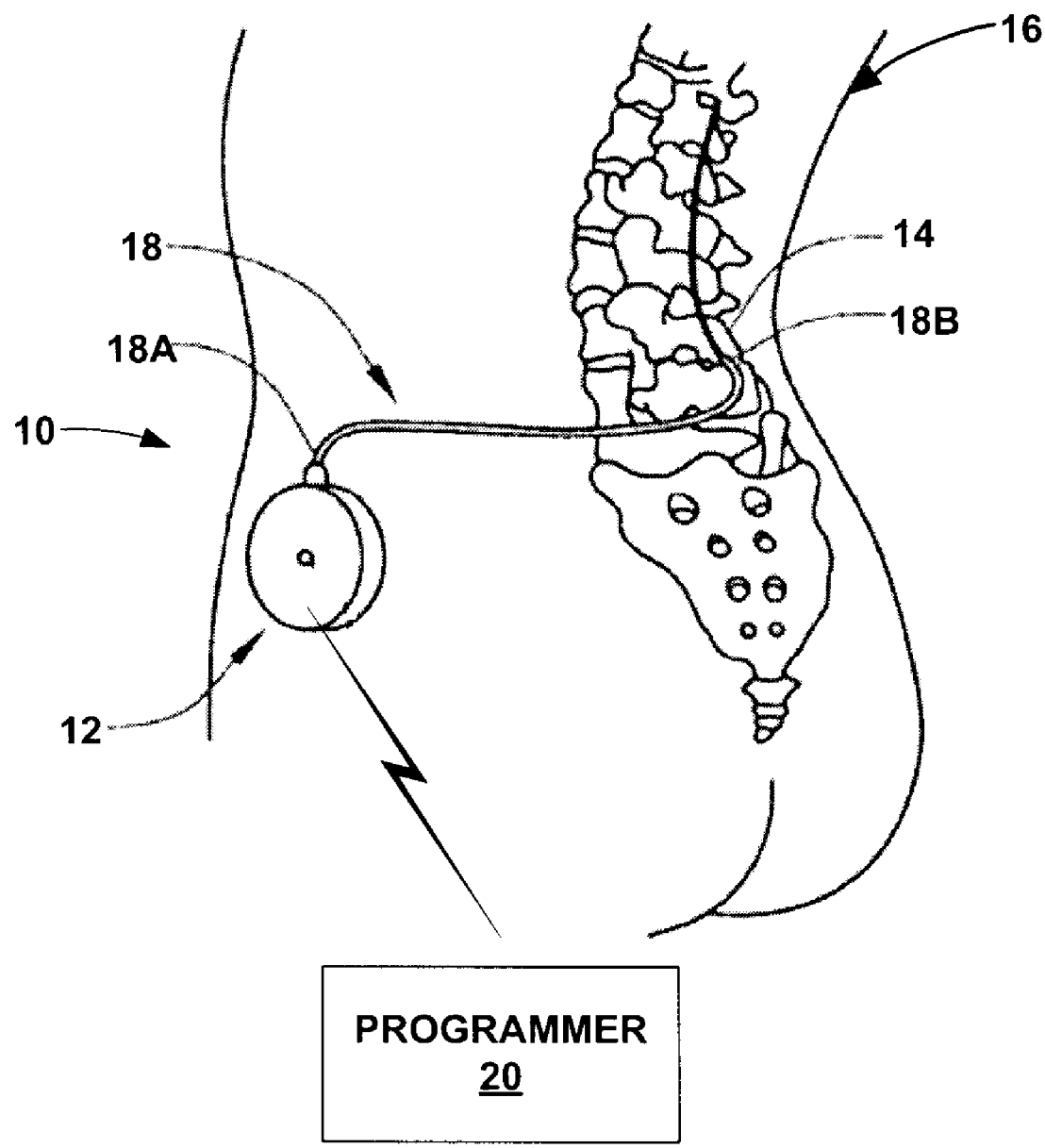
FIG. 1 is a conceptual diagram illustrating an embodiment of a fluid delivery system, which includes an implantable medical device that is configured to deliver a therapeutic agent to a patient via a catheter.

FIG. 1 is a conceptual diagram illustrating an embodiment of a therapy system 10, which includes IMD 12 configured to deliver at least one therapeutic agent, such as a pharmaceutical agent, insulin, pain relieving agent, anti-inflammatory agent, gene therapy agent, or the like, to a target tissue site within patient 16 via catheter 18, which is coupled to IMD 12. In the embodiment shown in FIG. 1, the target tissue site is proximate to spinal cord 14 of patient 16. A proximal end 18A of catheter 18 is coupled to IMD 12, while a distal end 18B of catheter 18 is located proximate to the target tissue site. Therapy system 10 also includes external programmer 20, which wirelessly communicates with IMD 12 as needed, such as to provide or retrieve therapy information or control aspects of therapy delivery (e.g., modify the therapy parameters, turn IMD 12 on or off, and so forth). While patient 16 is generally referred to as a human patient, other mammalian or non-mammalian patients are also contemplated.

Generally, IMD 12 has an outer housing that is constructed of a biocompatible material that resists corrosion and degradation from bodily fluids, such as titanium or biologically inert polymers. IMD 12 may be implanted within a subcutaneous pocket close to the stimulation site. For example, in the embodiment shown in FIG. 1, IMD 12 is implanted within an abdomen of patient 16. In other embodiments, IMD 12 may be implanted within other suitable sites within patient 16, which may depend, for example, on the target tissue site within patient 16 for the delivery of the therapeutic agent.

Catheter 18 may be coupled to IMD 12 either directly or with the aid of an extension (not shown in FIG. 1). In the embodiment shown in FIG. 1, catheter 18 traverses from the implant site of IMD 12 to one or more target tissue sites proximate to spine 14. Catheter 18 is positioned such that one or more fluid delivery outlets of catheter 18 are proximate to the one or more target tissue sites within patient 16. IMD 12 delivers a therapeutic agent to the one or more target tissue sites proximate to spinal cord 14 with the aid of catheter 18. For example, IMD 12 may be configured for intrathecal drug delivery into the intrathecal space or epidural space surrounding spinal cord 14. The intrathecal space is within the subarachnoid space of spinal card 14, which is past the epidural space and dura mater and through the theca of spinal cord 14.

Therapy system 10 may be used, for example, to reduce pain experienced by patient 16. IMD 12 may deliver one or more therapeutic agents to patient 16 according to one or more therapy program that sets forth different therapy parameters, such as bolus size, concentration of the therapeutic agent in each bolus, frequency of bolus delivery, and so forth. In some embodiments, the therapeutic agent may be a liquid. The therapy programs may be may be a part of a program group for therapy, where the group includes a plurality of therapy programs. In some embodiments, IMD 12 is configured to deliver a therapeutic agent to patient 16 according to different therapy programs that are selected based on a position (e.g., posture) of patient 16, an activity rate of patient 16 or other suitable patient parameters. IMD 12 may include a memory to store one or more therapy programs, instructions defining the extent to which patient 16 may adjust therapy parameters, switch between programs, or undertake other therapy adjustments. Patient 16 may select and/or generate additional therapy programs for use by IMD 12 via external programmer 20 at any time during therapy or as designated by the clinician.

In some embodiments, multiple catheters 18 may be coupled to IMD 12 to target the same or different tissue sites within patient 16. Thus, although a single catheter 18 is shown in FIG. 1, in other embodiments, system 10 may include multiple catheters or catheter 18 may define multiple lumens for delivering different therapeutic agents to patient 16 or for delivering a therapeutic agent to different tissue sites within patient 16. Accordingly, in some embodiments, IMD 12 may include a plurality of reservoirs for storing more than one type of therapeutic agent. However, for ease of description, an IMD 12 including a single reservoir is primarily discussed herein.

As described in further detail below, IMD 12 includes a tilt detector that provides information about the orientation of at least a portion of IMD 12, such as a fill port for a fluid reservoir within IMD 12. The orientation may be, for example, the direction in which the portion of the IMD 12 is facing relative to a reference point, which may be a baseline orientation of IMD 12 or an orientation of another tilt detector. The degree of tilt of IMD 12 within patient 16 relative to, for example, an epidermis of patient 16, may affect the orientation of the portion of the IMD 12. Thus, the orientation may also be referred to as the "tilt" of the portion of the IMD 12.

The tilt detector of IMD 12 may provide a digital or analog output, which may be converted to a digital output, if desired. The information from the tilt detector may be used to help align a medical instrument with the portion of IMD 12. For example, in some techniques for filling a reservoir of IMD 12 with a therapeutic agent or otherwise accessing the reservoir through a fill port, it may be desirable to orient a needle such that its longitudinal axis is substantially perpendicular to the fill port opening of IMD 12. As described in further detail below, such an orientation between the needle and fill port opening may help maximize the number of locations at which the needle may successfully enter the fill port and minimize the possibility of damaging the needle by, for example, missing the fill port opening and contacting an outer housing of IMD 12.

In some embodiments, the tilt detector may be an accelerometer (e.g., one-axis, two-axis or three axis accelerometers) or a system that determines an orientation of the portion of IMD 12 relative to a reference point based on fluctuating magnetic fields, which is similar to systems used in surgical navigation techniques. In the magnetic field-based orientation systems, a plurality of transmitter coils oriented in different directions may be associated with IMD 12, where at least some of the coils transmit signals at different frequencies to provide a coordinate system in space of fluctuating magnetic fields. An exterior orientation device may include a receiver coil that senses the magnetic fields and determines the relative orientation of IMD 12 within space based on the known orientation of the transmitter coils and the strength of the sensed magnetic fields.

Programmer 20 is an external computing device that is configured to wirelessly communicate with IMD 12. For example, programmer 20 may be a clinician programmer that the clinician uses to communicate with IMD 12. Alternatively, programmer 20 may be a patient programmer that allows patient 16 to view and modify therapy parameters. The clinician programmer may include more programming features than the patient programmer. In other words, more complex or sensitive tasks may only be allowed by the clinician programmer to prevent patient 16 from making undesired changes to IMD 12.

Programmer 20 may be a hand-held computing device that includes a display viewable by the user and a user input mechanism that can be used to provide input to programmer 20. For example, programmer 20 may include a small display screen (e.g., a liquid crystal display or a light emitting diode display) that presents information to the user. In addition, programmer 20 may include a keypad, buttons, a peripheral pointing device, touch screen or another input mechanism that allows the user to navigate though the user interface of programmer 20 and provide input.

If programmer 20 includes buttons and a keypad, the buttons may be dedicated to performing a certain function, i.e., a power button, or the buttons and the keypad may be soft keys that change in function depending upon the section of the user interface currently viewed by the user. Alternatively, the screen (not shown) of programmer 20 may be a touch screen that allows the user to provide input directly to the user interface shown on the display. The user may use a stylus or their finger to provide input to the display.

In other embodiments, rather than being a handheld computing device or a dedicated computing device, programmer 20 may be a larger workstation or a separate application within another multi-function device. For example, the multi-function device may be a cellular phone or personal digital assistant that can be configured to an application to simulate programmer 20. Alternatively, a notebook computer, tablet computer, or other personal computer may enter an application to become programmer 20 with a wireless adapter connected to the personal computer for communicating with IMD 12.

When programmer 20 is configured for use by the clinician, programmer 20 may be used to transmit initial programming information to IMD 12. This initial information may include system 10 hardware information such as the type of catheter 18, the position of catheter 18 within patient 16, the type of therapeutic agent(s) delivered by IMD 12, a baseline orientation of at least a portion of IMD 12 relative to a reference point, therapy parameters of therapy programs stored within IMD 12 or within programmer 20, and any other information the clinician desires to program into IMD 12.

The clinician also uses programmer 20 to program IMD 12 with one or more therapy programs, defined as programs that define the therapy delivered by IMD 12. During a programming session, the clinician may determine one or more therapy programs that may provide effective therapy to patient 16. Patient 16 may provide feedback to the clinician as to the efficacy of the specific program being evaluated. Once the clinician has identified one or more programs that may be beneficial to patient 16, patient 16 may continue the evaluation process and determine which program best alleviates the condition of patient 16 or otherwise provides efficacious therapy to patient 16. The therapy programs may set forth therapy parameters, such as different dosages of the therapeutic agent (e.g., a bolus size or concentration), the rate of delivery of the therapeutic agent, the maximum acceptable dose in each bolus, a time interval at which a dose of the therapeutic agent may be delivered to a patient 16 (lock-out interval), and so forth. IMD 12 may include a feature that prevents dosing the therapeutic agent in a manner inconsistent with the therapy program. Programmer 20 may assist the clinician in the creation/identification of therapy programs by providing a methodical system of identifying potentially beneficial therapy parameters.

Programmer 20 may also be configured for use by patient 16. When configured as the patient programmer, programmer 20 may have limited functionality in order to prevent patient 16 from altering critical functions or applications that may be detrimental to patient 16. In this manner, programmer 20 may only allow patient 16 to adjust certain therapy parameters or set an available range for a particular therapy parameter. Programmer 20 may also provide an indication to patient 16 when therapy is being delivered or when IMD 12 or when the power source within programmer 20 or IMD 12 need to be replaced or recharged.

Whether programmer 20 is configured for clinician or patient use, programmer 20 may communicate to IMD 12 or any other computing device via wireless communication. Programmer 20, for example, may communicate via wireless communication with IMD 12 using radio frequency (RF) telemetry techniques known in the art. Programmer 20 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 20 may also communicate with another programming or computing device via exchange of removable media, such as magnetic or optical disks, or memory cards or sticks. Further, programmer 20 may communicate with IMD 12 and other another programmer via remote telemetry techniques known in the art, communicating via a local area network (LAN), wide area network (WAN), public switched telephone network (PSTN), or cellular telephone network, for example.

In other applications of therapy system 10, the target therapy delivery site within patient 16 may be a location proximate to sacral nerves (e.g., the S2, S3 or S4 sacral nerves) in patient 16 or any other suitable nerve, organ, muscle or muscle group in patient 16, which may be selected based on, for example, a patient condition. For example, therapy system 10 may be used to deliver a therapeutic agent to tissue proximate to a pudendal nerve, a perineal nerve or other areas of the nervous system, in which cases, catheter 18 would be implanted and substantially fixed proximate to the respective nerve. As further examples, catheter 18 may be positioned to deliver a therapeutic agent to help manage peripheral neuropathy or post-operative pain mitigation, ilioinguinal nerve stimulation, intercostal nerve stimulation, gastric stimulation for the treatment of gastric mobility disorders and obesity, muscle stimulation, for mitigation of other peripheral and localized pain (e.g., leg pain or back pain). As another example, catheter 18 may be positioned to deliver a therapeutic agent to a deep brain site or within the heart (e.g., intraventricular delivery of the agent). Delivery of a therapeutic agent with the brain may help manage any number of neurological disorders or diseases. Example neurological disorders may include depression or other mood disorders, dementia, obsessive-compulsive disorder, migraines, obesity, and movement disorders, such as Parkinson's disease, spasticity, and epilepsy. Catheter 18 may also be positioned to deliver insulin to a patient with diabetes.

Examples of therapeutic agents IMD 12 may be configured to deliver include, but are not limited to, insulin, morphine, other pain mitigating pharmaceutical agents, genetic agents, antibiotics, nutritional fluids, analgesics, hormones or hormonal drugs, gene therapy drugs, anticoagulants, cardiovascular medications or chemotherapeutics.

Figure 2:
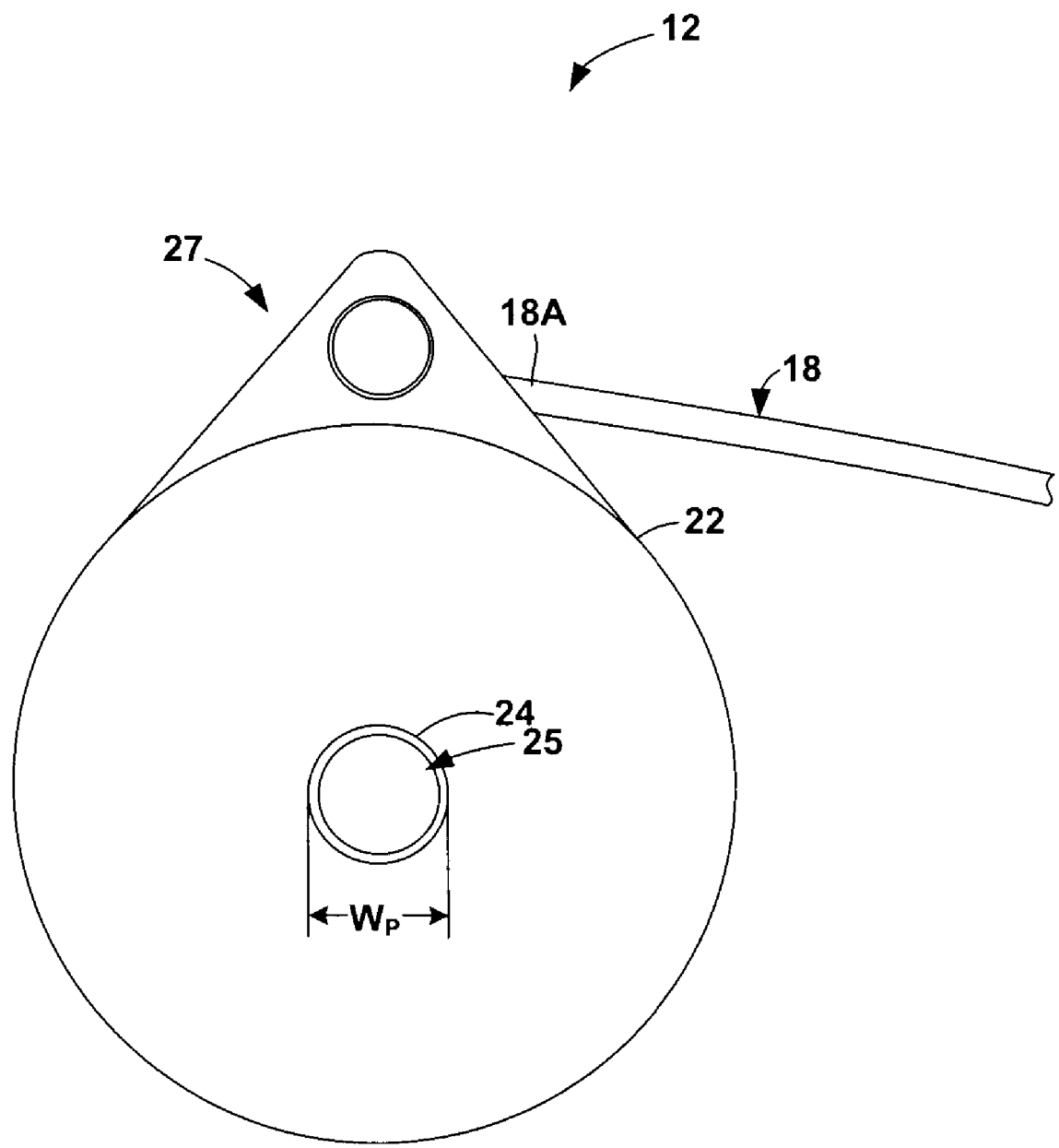
FIG. 2 is a schematic plan view of the implantable medical device of FIG. 1.

FIG. 2 is a schematic plan view of IMD 12, which includes an outer housing 22 defining an opening 24 through which fill port assembly 25 is accessible. IMD 12 also includes catheter access port assembly 27. Fill port assembly 25 and catheter port assembly 27 are configured to be accessed percutaneously when IMD 12 is implanted within patient 16. As described in further detail below, fill port assembly 25 provides access to a reservoir that retains a therapeutic agent. Catheter 18 is mechanically coupled to IMD 12 via catheter port assembly 27, which provides a sealed structure through which fluid may be directly passed to catheter 18 from a reservoir within IMD 12.

Figure 3:
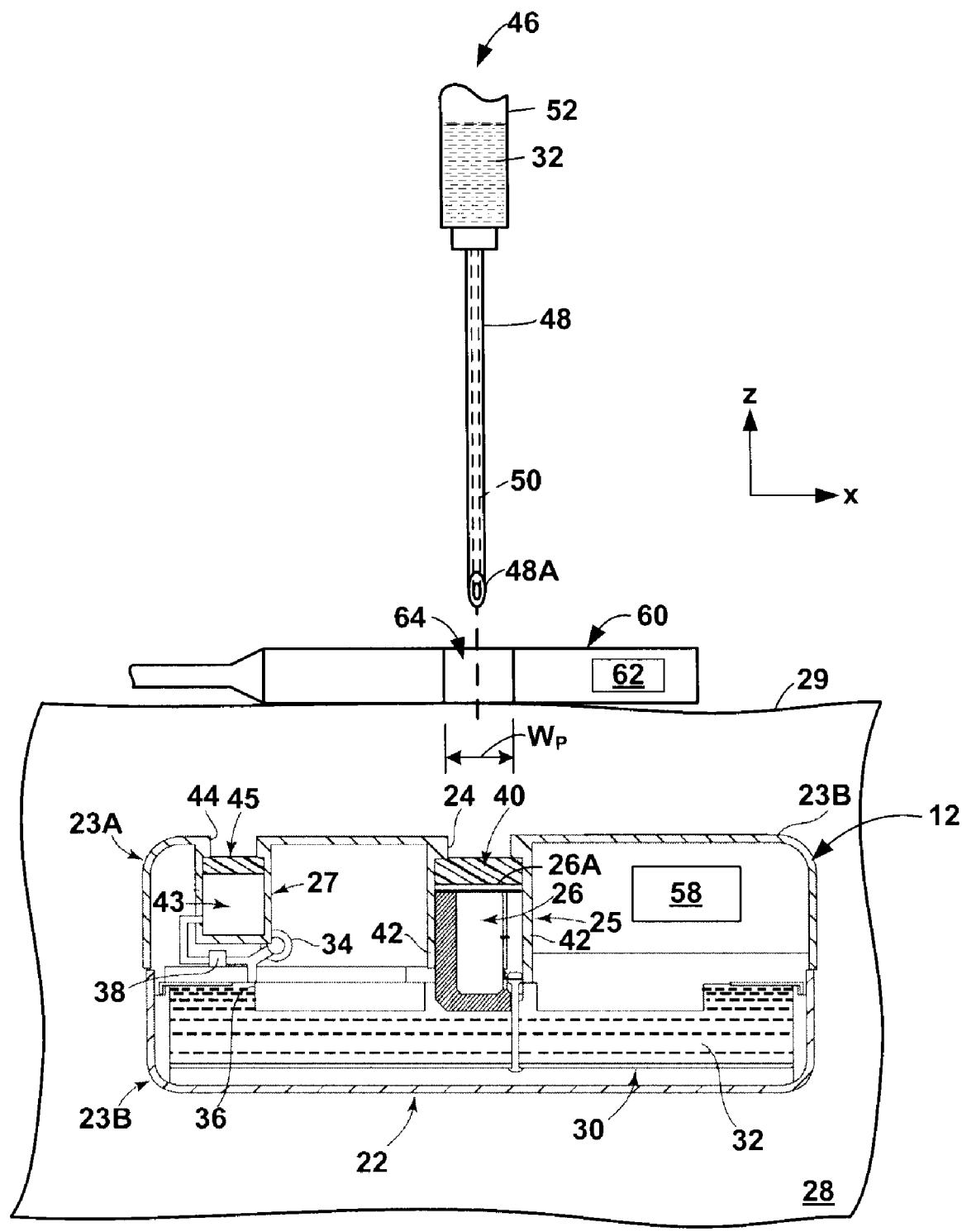
FIG. 3 is a schematic cross-sectional side view of the implantable medical device of FIG. 1 implanted within tissue of a patient.

FIG. 3 is a schematic cross-sectional illustration of IMD 12 implanted within tissue 28 of patient 16. Tissue 28 may be, for example, a subcutaneous tissue layer. In the embodiment shown in FIG. 3, housing 22 of IMD 12 includes first section 23A and second section 23B, which are coupled together and define an exterior surface of IMD 12. When assembled, first and second housing sections 23A, 23B contain reservoir 30, which stores therapeutic agent 32. Therapeutic agent 32 is delivered to a target tissue site within patient 16 via catheter 18 (FIG. 2). Housing 22 also includes discharge outlet 34 that is in fluid communication with a proximal end 18A of catheter 18 (FIG. 2). Reservoir outlet 36 of IMD 12 fluidically connects reservoir 30 and discharge outlet 34, thereby providing a pathway for therapeutic agent 32 to flow from reservoir 30 to discharge outlet 34, and through catheter 18 to the target tissue site within patient 16. In some embodiments, reservoir 30 may include a mechanism, such as a bellows system, to facilitate continuous, positive availability of therapeutic substance 32 at reservoir outlet 36. Further, in some embodiments, IMD 12 may include metering mechanism 38 that helps control a flow of therapeutic agent 32 from reservoir outlet 36 to discharge outlet 34.

Fill port assembly 25 may be useful for accessing reservoir 30 from outside of IMD housing 22. In particular, fill port assembly 25 provides a pathway for accessing reservoir 30 from an exterior side of housing 22. Fill port assembly 25 provides a sealed structure through which the reservoir 30 can be percutaneously accessed via the opening 24 in housing 22 (e.g., for filling the reservoir 30). Fill port assembly 25 includes fill port 26, which may be sealed from contaminants with the aid of septum 40. In some embodiments, septum 40 may be, for example, a self-sealing rubber membrane. Port wall 42 defines port 26, which is configured to communicate with an exterior of IMD 12 at fill port opening 26A.

Catheter access port assembly 27 provides a sealed structure through which fluid may be directly passed to catheter 18 (FIGS. 1-2) via discharge outlet 34. Catheter access port assembly 27 includes well 43, which is accessible from an exterior side of housing 22 through catheter access port opening 44. Catheter access port assembly 27 defines an opening that receives catheter 18, and mechanically couples to a proximal end of catheter 18A and fluidically couples catheter 18 to fluid within reservoir 30. Well 43 is in fluid communication with discharge outlet 34, e.g., with the aid of a fluid pathway. Well 43 may be sealed from contaminants with the aid of septum 45, which may be similar to septum 40 of fill port assembly 25. Septums 40, 45 may be formed of a resilient, resealable material, such as silicone rubber, that is durable enough to withstand numerous percutaneous hypodermic needle punctures without leaking.

After IMD 12 is implanted within patient 16, it may be desirable to access reservoir 30 in order to refill therapeutic agent 32 if the level of therapeutic agent 32 stored within reservoir 30 falls below a threshold, change the therapeutic agent stored within reservoir 30, flush reservoir 30, and so forth. For example, reservoir 30 may be refilled every few weeks or every few months, depending upon the capacity of reservoir 30 and the desirable agent delivery rate for patient 16. It may be desirable to percutaneously access to reservoir 30 in order to avoid surgical techniques for accessing reservoir 30. As described in further detail below, the alignment system described herein may facilitate the percutaneous introduction of a medical instrument into fill port 26 by providing information relating to the orientation of fill port opening 26A within tissue 28. For example, the alignment system may provide information to a user that indicates the direction the fill port opening 26A is facing within tissue 28 relative to skin surface 29.

As shown in FIG. 3, after IMD 12 is implanted within tissue 28, a clinician may locate septum 40. The clinician may locate septum 40 with the aid of a locating technique, such as those described in U.S. Pat. No. 7,806,122 to Hoendervoogt et al. which issued on Oct. 5, 2010, and is entitled, "SEPTUM PORT LOCATOR SYSTEM AND METHOD FOR AN IMPLANTABLE THERAPEUTIC SUBSTANCE DELIVERY DEVICE", which is incorporated herein by reference in its entirety. In one technique described by U.S. Pat. No. 7,806, 122 to Hoendervoogt et al., a coil is located at a known position relative to fill port opening 26A. An external locator device includes a controller and a locator grid that has at least one X-loop electrically coupled to the controller and oriented along a first major axis, and at least one Y-loop electrically coupled to the controller and oriented along a second major axis differing from (e.g., orthogonal to) the first major axis. When the locator grid is spatially proximate the coil of IMD 12, and the coil is energized, the energized coil induces a voltage in the Y-loop, which is read by the controller. The controller may then determine a location of the coil relative to the locator grid based upon the signal induced in the Y-loop, and locate the fill port opening 26A based upon the determined location of the coil. Other techniques for locating septum 40 and fill port opening 26A of IMD 12 may also be used.

After locating septum 40, the clinician may align medical instrument 46 with fill port opening 26A and introduce medical instrument 46 through septum 40 to gain access to reservoir 30. In the embodiment shown in FIG. 3, medical instrument 46 includes needle 48 defining an inner lumen 50 and a compartment 52 that retains a therapeutic agent 32, which may be, for example, in a fluid state. Compartment 52 may be, for example, a barrel of a syringe or another enclosed space that receives and retains a fluid. Needle 48 may be, for example, a hypodermic needle or another instrument that may be used to pierce through epidermis 29 and septum 40 and deliver therapeutic agent 32 into reservoir 30. In this manner, reservoir 30 may be percutaneously accessed by inserting needle 48 through the patient's epidermis 29, through fill port opening 26A and septum 40. Once needle 48 punctures septum 40, therapeutic agent 32 may be released through inner lumen 50 of needle 48 and into reservoir 30. Similarly, percutaneous direct delivery of liquid to the patient 16 may be accomplished by introducing a needle or another medical instrument through septum 45 and into well 43 of catheter access port assembly 27. Thus, a therapeutic agent may be introduced into reservoir 30 or may be delivered to catheter 18 by way of the catheter access port assembly 27. In particular, catheter access port assembly 27 provides a sealed structure through which fluid may be directly flowed to the discharge outlet 34 and to catheter 18, thereby effectively bypassing reservoir 30.

In the embodiment shown in FIG. 3, opening 24 defined by housing 22 and opening 26A of fill port 26 have substantially similar widths $W_P$. In other embodiments, however, opening 24 and opening 26A may be different sizes. For example, in some embodiments, opening 24 defined by housing 22 may define a greater width than opening 26A at the outer surface of housing 22, and opening 24 may include sidewalls that taper from the wider opening toward septum 40. The inclined sidewalls may help guide needle 48 into fill port 26.

Figure 4A:
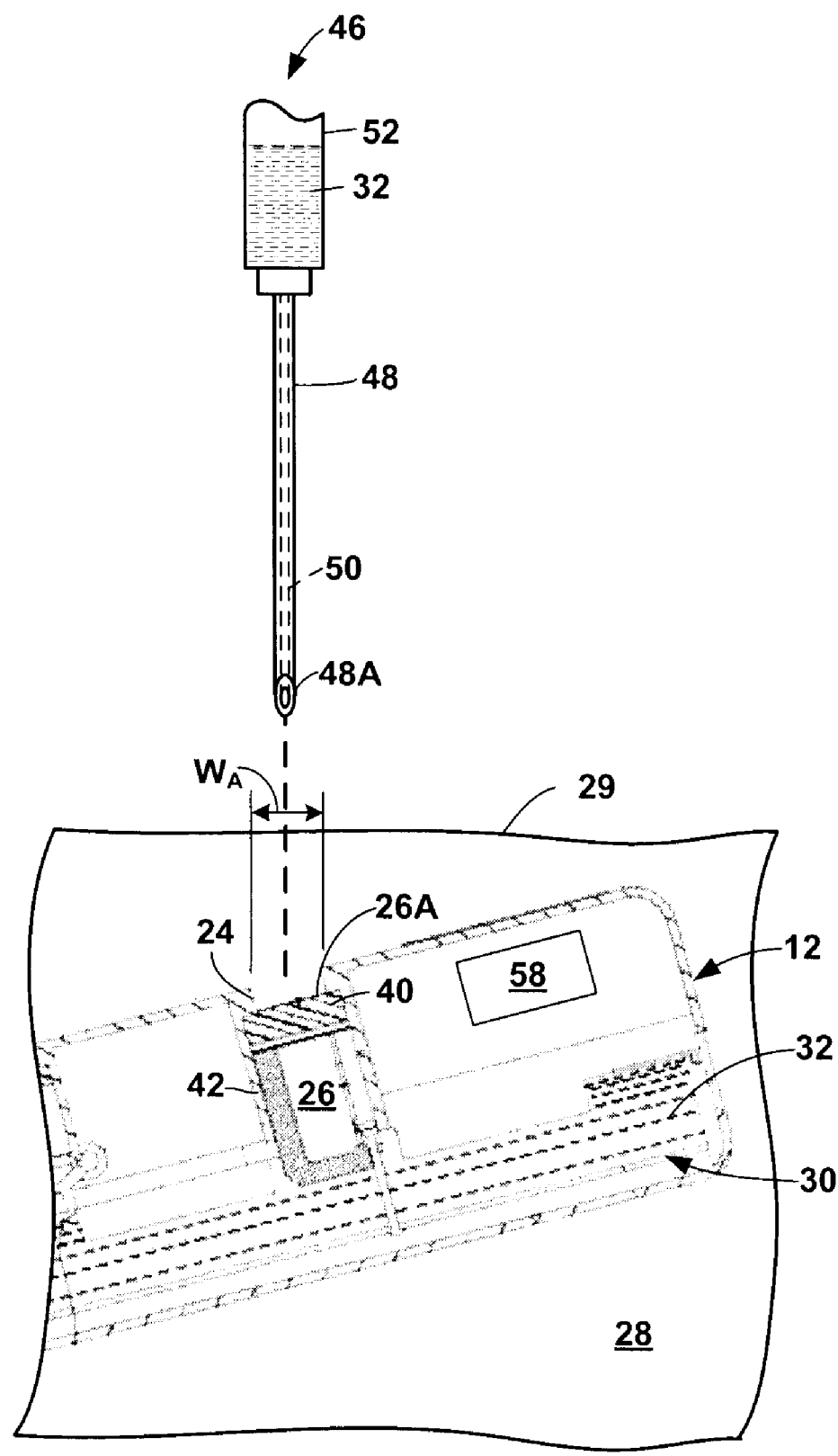
FIG. 4A is a schematic cross-sectional side view of the implantable medical device of FIG. 3, and further illustrates an orientation device and an external instrument.

As shown in FIG. 3, the range of locations at which needle 48 may enter fill port 26 may be maximized when needle 48 is positioned in a particular orientation relative to fill port opening 26A. In the embodiment shown in FIG. 3, the range of locations at which needle 48 may enter fill port 26 is substantially maximized when needle 48 is oriented substantially perpendicular to fill port opening 26A because needle 48 may enter fill port opening 26A at any location along the full width $W_P$ of fill port opening 26A. However, as shown in FIG. 4A, as IMD 12, and, therefore fill port opening 26A, changes angular position within tissue 28 and faces a different direction relative to epidermis 29, the range of locations at which needle 48 may enter fill port 26 may decrease if needle 48 remains substantially perpendicular to epidermis surface 29.

If IMD 12 changes angular position within tissue 28, needle 48 may no longer enter fill port opening 26A at any location along the full width $W_P$ of fill port opening 26A if needle 48 remains substantially perpendicular to epidermis surface 29 because the full width $W_P$ may no longer be toward needle 48. Instead, needle 48 may only access fill port opening 26A through an opening having an effective width $W_A$ that is smaller than width $W_P$ of fill port opening 26A, thereby limiting the range of locations at which needle 48 may be aligned with fill port 26.

It may be also be desirable to properly align needle 48 with port 26 in order to help minimize or even prevent damage to needle 48 and septum 40. For example, if needle 48 is introduced through septum 40 at a particular range of angles, needle 48 may damage septum 40 (e.g., septum 40 may lose its self-sealing attributes). As another example, tip 48A of needle 48 may break if it is incorrectly inserted into port 26 and contacts wall 42 of port 26, or if needle 48 contacts an outer housing 22 of IMD 12, which may be relatively hard. A broken needle tip 48A may be harmful to patient 16 if the broken portions remain within patient 16. In addition, a damaged needle tip 48A may damage septum 40. In addition, if needle 48 is not correctly aligned with fill port 26 and is inadvertently inserted into catheter access port 27 of IMD 12 or directly into tissue 28, therapeutic agent 32 may inadvertently be delivered directly into patient 16, thereby introducing a significant quantity of therapeutic agent 32 to patient 16, with potentially adverse consequences. Other problems may arise if needle 48 is not correctly aligned with fill port 26.

Figure 4B:
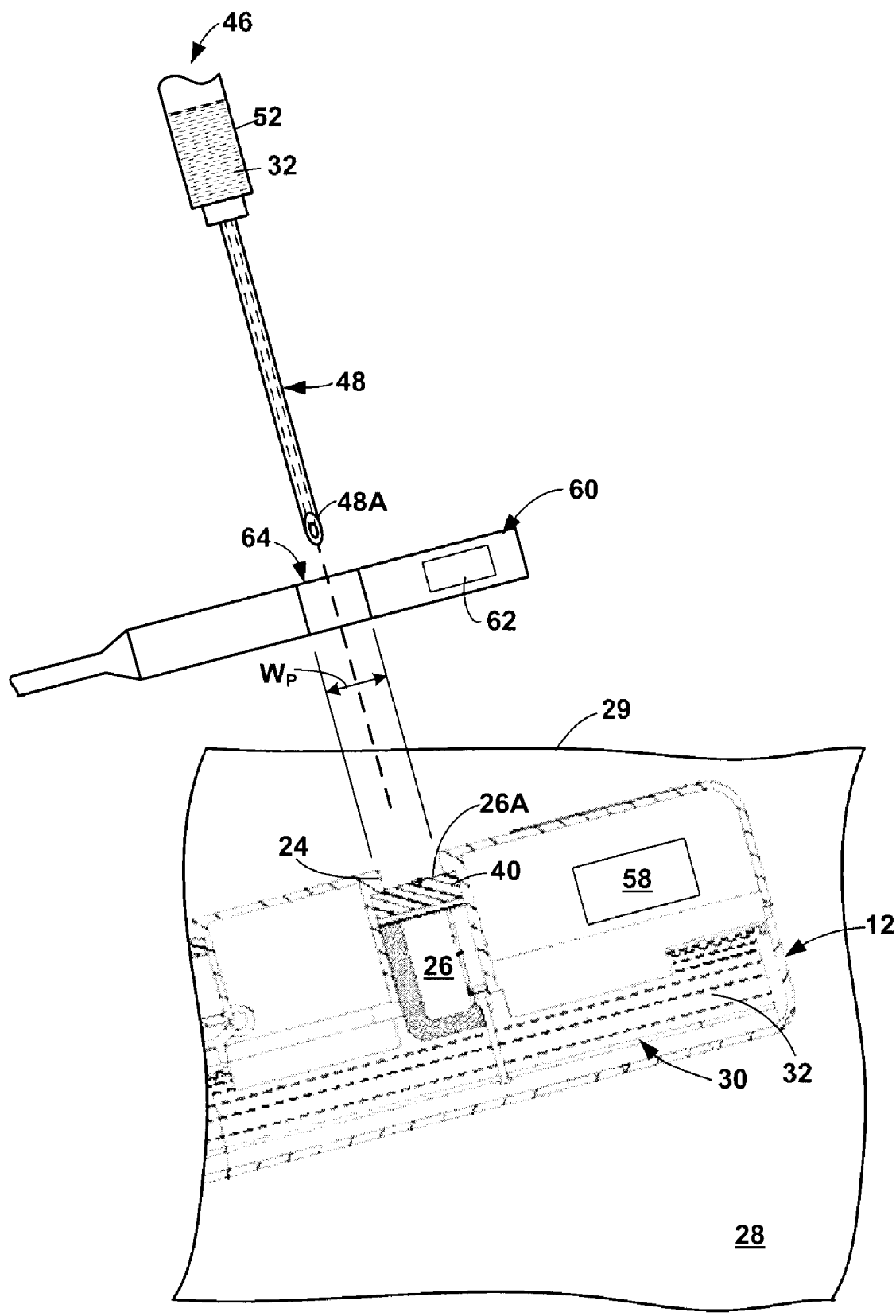
FIG. 4B is a schematic cross-sectional illustration of the implantable medical device of FIG. 3, where an external instrument is positioned to substantially match an orientation of a fill port opening of the implantable medical device.

For at least these reasons, it may be desirable for the clinician to orient (i.e., position or place) needle 48 relative to epidermis 29 based on the orientation of fill port opening 26A within tissue 28. For example, it may be desirable for the clinician to orient needle 48 such that its longitudinal axis is generally perpendicular to a major surface of septum 40 or generally parallel to wall 42 of fill port 26. Septum 40 may define a major surface regardless of whether septum 40 defines a generally planar surface. In other embodiments, it may be desirable for the clinician to orient needle 48 such that its longitudinal axis is oriented within a particular ranges of angles relative to the major surface of septum 40 or wall 42 of fill port 26. FIG. 4B illustrates a needle 48 that is oriented to substantially match the orientation of fill port 26, such that substantially the full width $W_P$ of port 26 is available for receiving needle 48, despite the angulation of IMD 12 within tissue 28.

In some cases, aligning the orientation of needle 48 of instrument 46 with the orientation of port 26 within tissue 28 may be relatively difficult because IMD 12 is implanted within patient 16 and is not visible to a clinician without the aid of medical imaging devices (e.g., X-ray or magnetic resonance imaging devices). In existing techniques for locating fill port 26 and determining an orientation of fill port opening 26A, a clinician may palpate tissue 28 near the IMD 12 implant site. That is, a clinician may manually feel tissue 28 (i.e., physically examine) near the IMD 12 implant site in order to determine a location of a part of IMD 12 that indicates the approximate location of fill port 26. For example, opening 24 in housing 22 of IMD 12 may feel different than the rest of housing 22, thus, the clinician may examine tissue 28 until opening 24 in housing 22 is felt. However, in some situations, such as in the case of relatively obese patients, the palpation technique may be ineffective in locating port 26 or determining the orientation of opening 26A. Depending on the implant site of IMD 12, the orientation of port 26 within tissue 28 may change over time, e.g., as patient 16 moves or as IMD 12 settles within tissue 28. Accordingly, even if IMD 12 is implanted in a known orientation within patient 16, the original location and orientation of port opening 26A may change over time. Thus, a physical marker, such as a tattoo marked on the patient's body, which indicates the location of port opening 26A may be ineffective in determining an orientation of port opening 26A relative to outer surface of epidermis 29 because even if IMD 12 remains in its original implanted position, port 26 may tilt or otherwise change orientation.

A tilt alignment system comprising a first tilt detector 58 associated with IMD 12 and a second tilt detector 62 associated with external instrument 46 may provide information indicative of the orientation of fill port opening 26A or another portion of IMD 12 within tissue 28. Thus, tilt detectors 58, 62 may help a clinician align needle 48 of instrument 46 with port 26 of IMD 12 prior to introduction of needle 48 into patient 16. In the embodiment shown in FIGS. 3-4B, tilt detector 62 is a part of orientation device 60, which includes a body that defines an aperture 64 configured to receive needle 48. As described in further detail below, a clinician may manipulate the position of orientation device 60 in order to generally match the orientation of aperture 64 with the orientation of fill port opening 26A. After orientation device 60 is positioned based on information from tilt detectors 58, 62, aperture 64 may help frame a region of epidermis 29 through which needle 48 may be introduced in order to access fill port 26, as well as indicate the general orientation of fill port opening 26A.

Tilt detector 58 is provided in a known orientation relative to fill port opening 26A. As a result, the orientation of fill port opening 26A relative to tilt detector 62 of orientation device 60 or another device may be determined based on information provided by tilt detector 58. In other words, information provided by tilt detector 58 may be processed to determine the general direction in which a major surface of septum 40 is facing relative to a reference point (e.g., tilt detector 62 or a baseline orientation of fill port opening 26A), i.e., to determine a tilt of IMD 12 within patient 16. Similarly, tilt detector 62 is provided in a known orientation relative to aperture 64. The orientation of aperture 64 relative to fill port opening 26A may be determined based on information provided by tilt detectors 58, 62.

Tilt detectors 58, 62 may each be, for example, an accelerometer (e.g., a one-axis, two-axis or three-axis accelerometer) or another device that provides measurable signals (e.g., electrical signals or magnetic fields) that change with the orientation of port opening 26A. In embodiments in which tilt detectors 58, 62 are accelerometers, tilt detectors 58, 62 each generate signals representative of acceleration vectors that indicate of the orientation of port opening 26A or orientation device 60, respectively, relative to a primary acceleration vector, which may be a gravity vector.

Tilt detectors 58, 62 have a common primary acceleration vector. Thus, the outputs from tilt detectors 58, 62 are calibrated with each other. That is, the signals from tilt detectors 58, 62 indicate the relative orientation of the tilt detectors 58, 62 with respect to a common reference, and, therefore, output from tilt detectors 58, 62 have a known relationship relative to each other. Tilt detectors 58, 62 may be positioned within IMD 12 and orientation device 60, respectively, such that the output from tilt detectors 58, 62 generally matches when the orientation of aperture 64 substantially aligns with the orientation of fill port opening 26A, as shown in FIGS. 3 and 4B, and aperture 64 generally frames width $W_P$ of fill port opening 26A.

In embodiments in which tilt detectors 58, 62 are each three-axis accelerometers, tilt detectors 58, 62 provides information, e.g., in the form of electrical signals, that indicate the orientation of fill port opening 26A and aperture 64, respectively, in three directions, i.e., orthogonal x-axis, y-axis, and z-axis directions (orthogonal x-z axes are shown in FIG. 3). The x-axis may correspond to, for example, the pitch of fill port opening 26A relative to aperture 64, the y-axis direction may correspond to the yaw of fill port opening 26A relative to aperture 64, and the z-axis direction may correspond to the roll of fill port opening 26A relative to aperture 64. In some embodiments, signals from tilt detectors 58, 62 may be processed to determine values indicative of the x-axis, y-axis, and z-axis force vectors (e.g., acceleration vectors in the case of an accelerometer), where the values assume that the earth's gravity is the primary acceleration vector.

IMD 12 may wirelessly transmit signals from tilt detector 58 to orientation device 60. Orientation device 60 may receive the signals from tilt detector 58 and a processor within orientation device 60 may employ different techniques to determine when an orientation of aperture 64 of orientation device 60 substantially matches an orientation of fill port opening 26A. In one technique, the processor may determine when the output of tilt detectors 58, 62 substantially match (e.g., exactly match or are within a predetermined range), which indicates that aperture 64 and fill port opening 26A are oriented substantially similarly. The predetermined range of acceptable differences in the output of tilt detectors 58, 62 may be selected based on, for example, an acceptable range of orientations at which needle 48 may enter fill port opening 26A without breaking tip 48A or substantially damaging tip 48A.

In one embodiment, based on information from tilt detectors 58, 62, a user (e.g., a clinician) may change the orientation of orientation device 60 relative to the patient's epidermis surface 29 until an orientation of aperture 64 of orientation device 60 substantially matches the orientation of the opening of port 26. The processor of orientation device 60 may then control an indicator to alert the user when the output of tilt detectors 58, 62 substantially match, thereby indicating orientation device 60 is properly oriented relative to fill port opening 26A. By indicating the orientation of fill port opening 26A, orientation device 60 may help maximize the locations at which needle 48 may be introduced into port 26.

As another example of a technique for determining when an orientation of aperture 64 of orientation device 60 substantially matches an orientation of fill port opening 26A, the processor may analyze the offset between the outputs between tilt detectors 58, 62 to determine the relative orientation between aperture 64 and fill port opening 26A. The relative orientation between aperture 64 and fill port opening 26A generally refers to the position of aperture 64 (e.g., a major surface of device 60 defining aperture 64) relative to the position of fill port opening 26A (or the fill port opening 26A relative to aperture 64). In addition, the relative orientation between aperture 64 and fill port opening 26A may also indicate the direction in which fill port opening 26A may be facing within tissue 28 (i.e., a "tilt" of fill port opening 26A) relative to epidermis 29.

Based on the determined offsets in tilt detector outputs, the processor may guide a user to position device 60 such that the orientation of aperture 64 substantially matches an orientation of fill port opening 26A. Tilt detector 62 may output signals (X1, Y1, Z1) that indicate the acceleration vectors in the x-axis, y-axis, and z-axis directions relative to a primary acceleration vector.

Tilt detector 58 may output signals (X2, Y2, Z2) that indicate the acceleration vectors in the x-axis, y-axis, and z-axis directions relative to the same primary acceleration vector as tilt detector 62. The offset between the outputs of tilt detectors 58, 62 may be, for example, (X1-X2, Y1-Y2, Z1-Z2). In embodiments in which tilt detectors 58, 62 are three-axis accelerometers, the processor may correlate a certain change in acceleration vectors with a certain magnitude of movement. For example, a certain change in the acceleration vector in the x-axis direction, ΔX, may be associated with a one centimeter movement in the positive x-axis direction. After determining the offset in acceleration vectors output by tilt detectors 58, 62, the processor may determine the direction and magnitudes of movement necessary to align the orientation of aperture 64 with fill port opening 26A.

In another technique for determining when an orientation of aperture 64 of orientation device 60 substantially matches an orientation of fill port opening 26A, the processor within orientation device 60 or another computing device may analyze the offset between the output of tilt detector 58 of IMD 12 and a baseline value to determine the orientation of fill port opening 26A relative to the baseline position. The baseline position may be a known position, e.g., an orientation of fill port opening 26A during implantation of IMD 12, i.e., prior to IMD 12 shifting positions. The baseline value may be the output of tilt detector 58 at the baseline position. In embodiments in which tilt detector 58 is a three-axis accelerometer, the processor of orientation device 60, IMD 12, or another device may correlate a certain change in acceleration vectors with a certain magnitude of movement. After determining the offset in acceleration vectors between the output of tilt detector 58 of IMD 12 and the baseline value, the processor may determine the extent to which fill port opening 26A changed orientation within tissue 28. Based on this information, the processor may determine the direction and magnitudes of movement necessary orient device 60 such that the orientation of aperture 64 substantially matches an orientation of fill port opening 26A.

Figure 5:
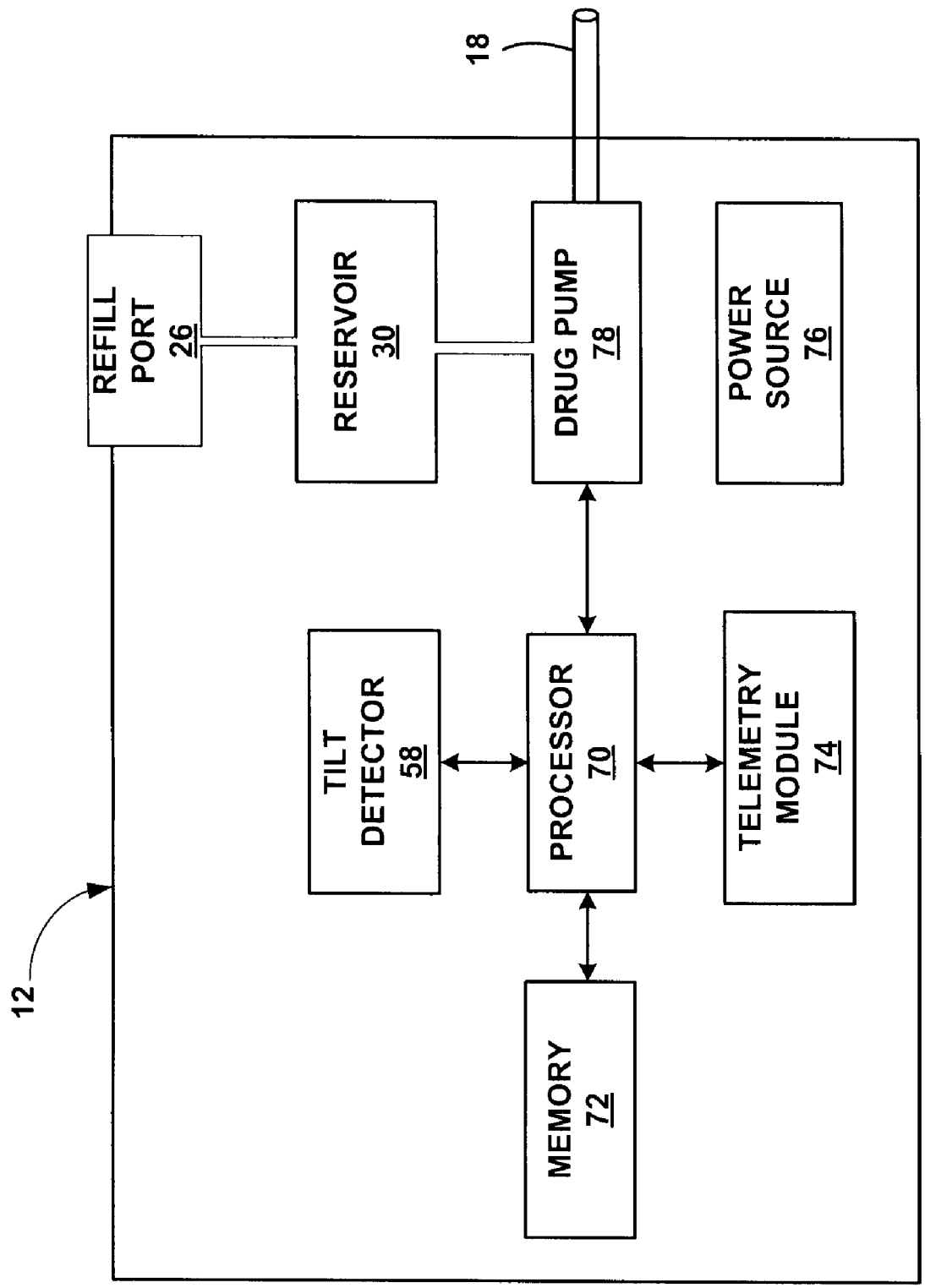
FIG. 5 is functional block diagram of an embodiment of an implantable medical device.

FIG. 5 is a functional block diagram illustrating components of an embodiment of IMD 12, which includes fill port 26, reservoir 30, tilt detector 58, processor 70, memory 72, telemetry module 74, power source 76, and drug pump 78. Processor 70 may include a microprocessor, a controller, a digital signal processor (DSP), an application specific integrated circuit (ASIC), a field-programmable gate array (FPGA), discrete logic circuitry, or the like. Drug pump 78 may be a mechanism that delivers a therapeutic agent in some metered or other desired flow dosage to the therapy site within patient 16 from reservoir 30 via the catheter 18 (shown in FIG. 2).

Processor 70 controls the operation of drug pump 78 with the aid of instructions that are stored in memory 72. For example, the instructions may define therapy programs that specify the bolus size of a therapeutic agent that is delivered to a target tissue site within patient 16 from reservoir 30 via catheter 18. The therapy programs may also include other therapy parameters, such as the frequency of bolus delivery, the concentration of the therapeutic agent delivered in each bolus, the type of therapeutic agent delivered if IMD 12 is configured to deliver more than one type of therapeutic agent), and so forth. In some embodiments, IMD 12 may also include an electrical stimulation generator for producing electrical stimulation in addition to delivering drug therapy.

Memory 72 may include any volatile or non-volatile media, such as a random access memory (RAM), read only memory (ROM), non-volatile RAM (NVRAM), electrically erasable programmable ROM (EEPROM), flash memory, and the like. Memory 72 may store instructions for execution by processor 70, such as, but not limited to, therapy programs, information utilized by processor 70 to translate output from tilt detector 58 to a useful format for determining a position of fill port 26 relative to a reference point, and any other information regarding therapy of patient 16. Memory 72 may include separate memories for storing instructions, patient information, therapy parameters (e.g., grouped into sets referred to as "therapy programs"), and other categories of information. In some embodiments, memory 72 stores program instructions that, when executed by processor 70, cause IMD 12 and processor 70 to perform the functions attributed to them herein.

Telemetry module 74 in IMD 12, as well as telemetry modules in other devices described herein, such as programmer 20, may accomplish communication by RF communication techniques. In addition, telemetry module 74 may communicate with programmer 20 via proximal inductive interaction of IMD 12 with external programmer 20. Accordingly, telemetry module 74 may send information to external programmer 20 on a continuous basis, at periodic intervals, or upon request from the implantable stimulator or programmer. Processor 70 controls telemetry module 74 to send and receive information. Wireless telemetry may be accomplished by RF communication or proximal inductive interaction of IMD 12 with external programmer 20.

Power source 76 delivers operating power to various components of IMD 12. Power source 76 may include a small rechargeable or non-rechargeable battery and a power generation circuit to produce the operating power. Recharging may be accomplished through proximal inductive interaction between an external charger and an inductive charging coil within IMD 12. In some embodiments, power requirements may be small enough to allow IMD 12 to utilize patient motion and implement a kinetic energy-scavenging device to trickle charge a rechargeable battery. In other embodiments, traditional batteries may be used for a limited period of time. As a further alternative, an external inductive power supply could transcutaneously power IMD 12 whenever measurements are needed or desired.

In the embodiment shown in FIG. 5, processor 70 is electrically coupled to tilt detector 58 such that processor 70 may receive electrical signals generated by tilt detector 58 e.g., via appropriate amplifier, filter, and analog-to-digital converter circuitry. As previously described, the electrical signals from tilt detector 58 may be used to determine the location and orientation of at least a portion of IMD 12, such as fill port opening 26A, relative to a reference point. The reference point may be, for example, tilt detector 62 of orientation device 60, a tilt detector within medical instrument 46, a tilt detector otherwise associated with instrument 46 or a baseline position of fill port opening 26A. Thus, in some cases, the reference point may be movable relative to patient 16 (e.g., instrument 46 or an indicator element that is separate from instrument 46).

Figure 8A:
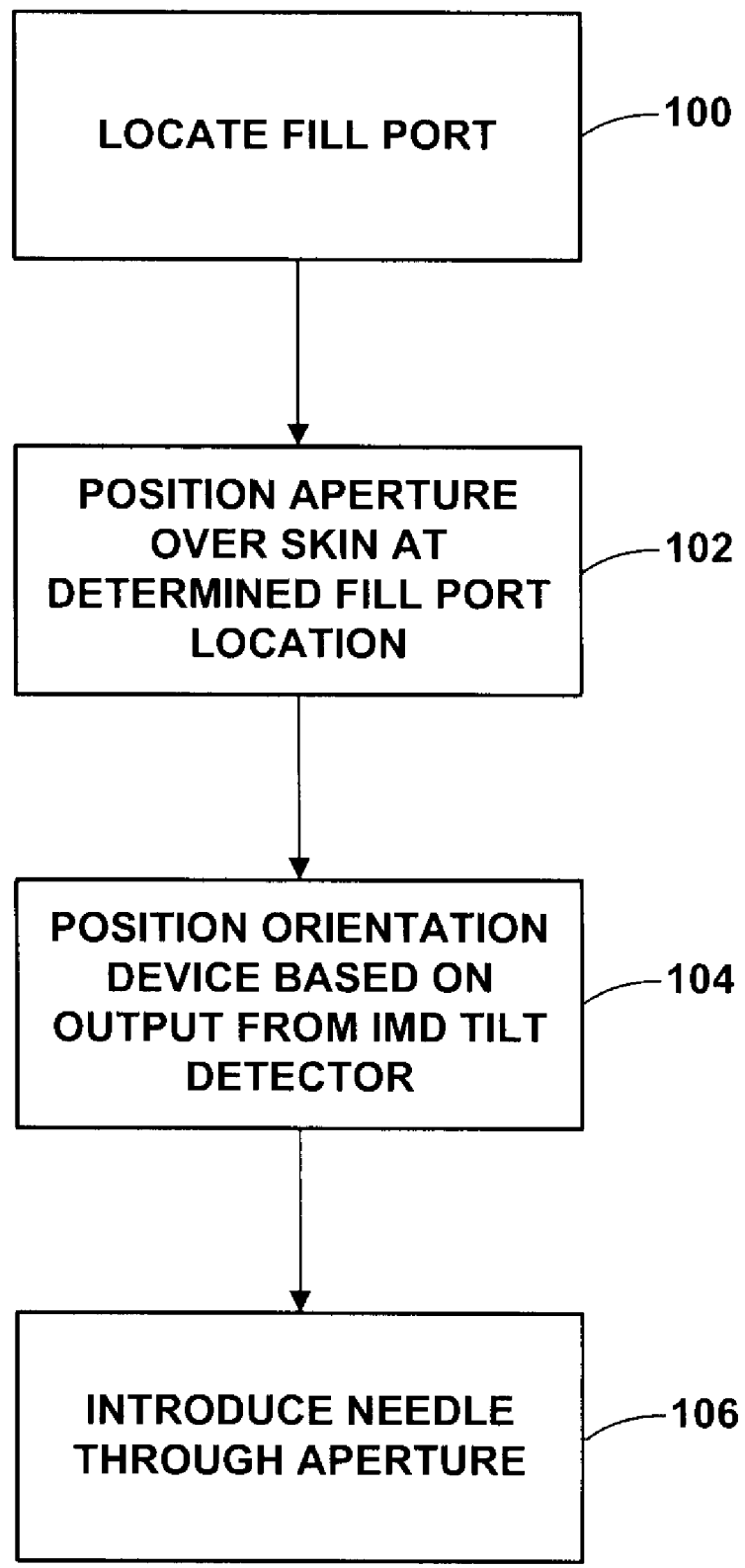
FIGS. 8A and 8B are flow diagrams illustrating embodiments of techniques for orienting a medical instrument relative to a portion of an implanted medical device with the aid of the orientation system shown in FIG. 3.
Figure 8B:
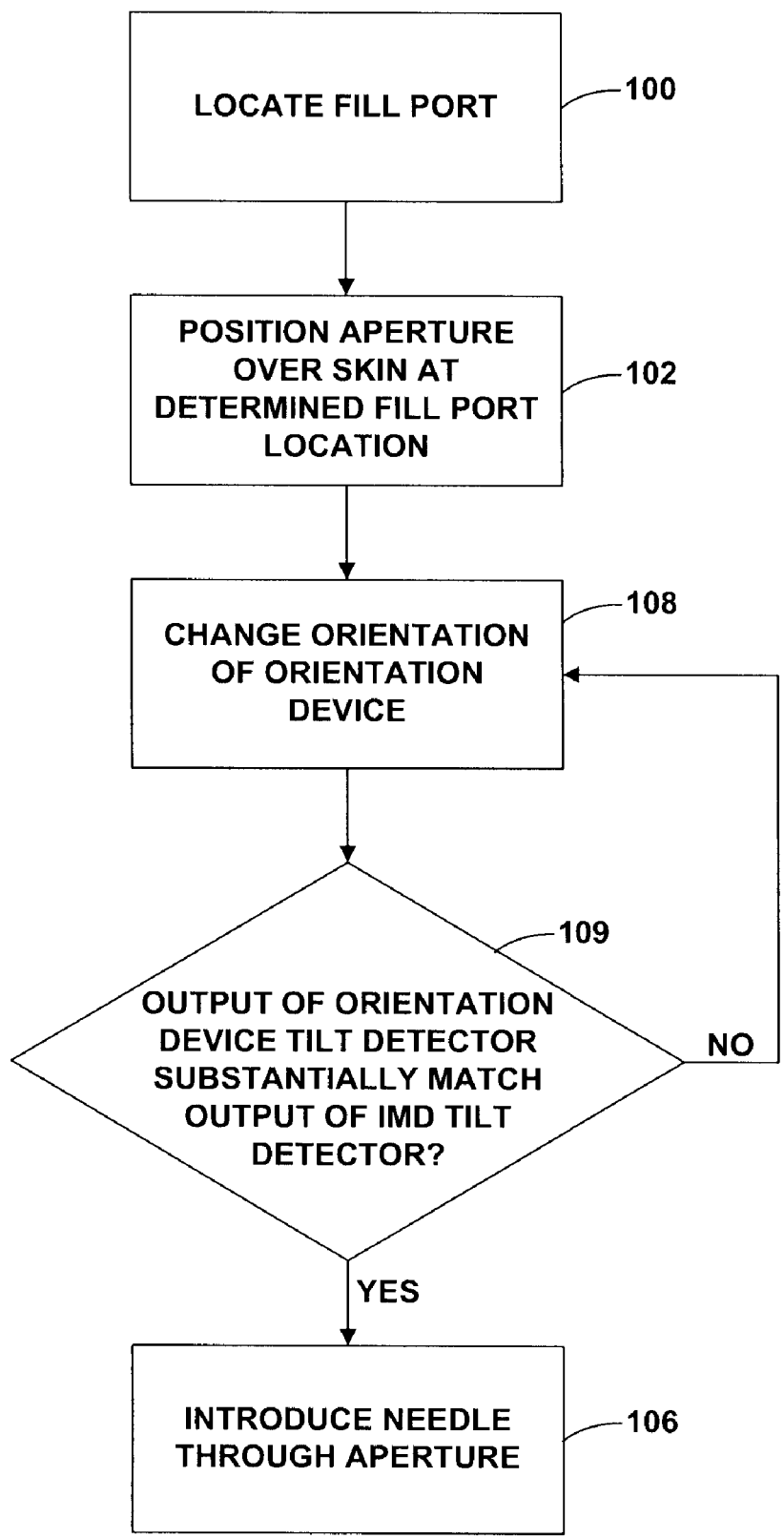
Figure 9:
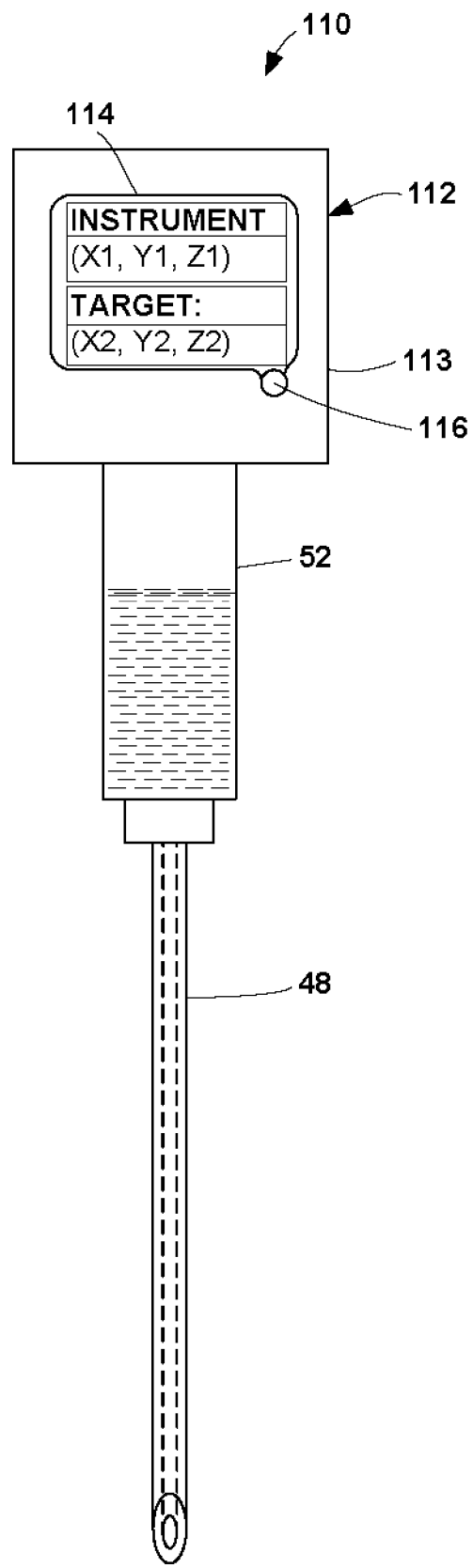
FIG. 9 is a schematic illustration of a medical instrument that includes an orientation device.

While the description of FIGS. 2-8 primarily discuss the reference point as being tilt detector 62 of orientation device 60, in other embodiments, the reference point may be incorporated within instrument 46, as described with respect to FIG. 9. In addition, while the remainder of the description of the invention is primarily directed to determining the orientation of fill port 26, in other embodiments, the orientations of other portions of IMD 12 may be determined with the aid of information from tilt detector 58 or another tilt detector that is in a known orientation relative to the other portions of IMD 12.

In some embodiments, processor 70 may receive signals from tilt detector 62 of orientation device 60 (e.g., via wireless telemetry techniques), and determine the orientation of fill port opening 26A of IMD 12 relative to the aperture 64 of orientation device 60 based on signals from tilt detectors 58, 62. Processor 70 may transmit the determined relative orientation of aperture 64 and fill port opening 26A to another device, such as orientation device 60, programmer 20 (FIG. 1) or instrument 46 (FIG. 3). The clinician may then orient device 60 based on the determined relative orientations of fill port opening 26A and aperture 64 of device 60.

For example, the clinician may orient aperture 64 of device 60 to substantially match the determined orientation of fill port 26. As described in further detail below, in some embodiments, orientation device 60 may include a display that may present instructions to the clinician relating to the direction and magnitudes of moving orientation device 60 in order to orient orientation device 60 in order to substantially align the tilt of aperture 64 with the tilt of fill port opening 26A. Alternatively, orientation device 60 may include an indicator, such as visible lights or sounds, which indicate when processor 70 has determined that an orientation of aperture 64 substantially matches fill port 26. Thus, the clinician may rotate device 60 until information (e.g., feedback) indicating a successful match is received.

Figure 6:
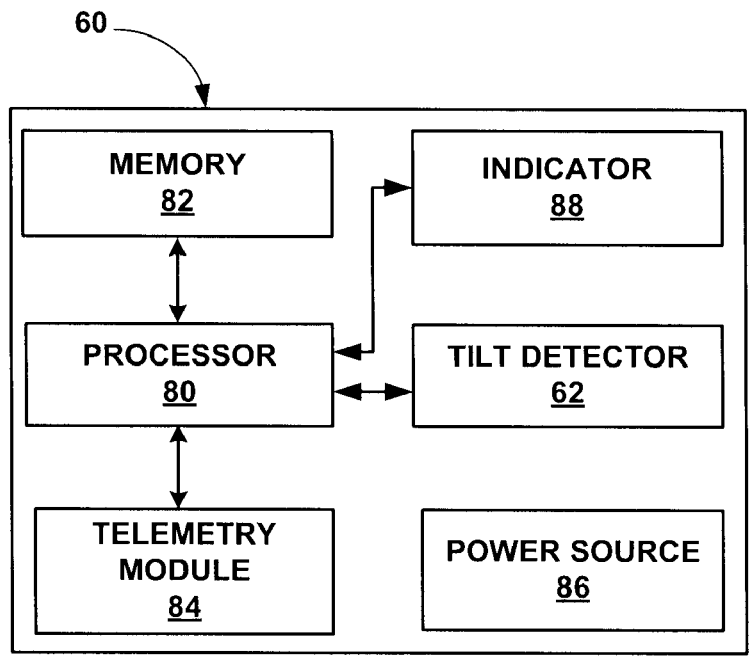
FIG. 6 is a functional block diagram of an embodiment of an orientation device.

Alternatively, processor 70 of IMD 12 may transmit the signals from tilt detector 58 to orientation device 60 by wireless telemetry, i.e., via telemetry module 74. Orientation device 60 may include a processor that determines a relative orientation between fill port 26 of IMD 12 and aperture 64 of orientation device 60. FIG. 6 is a functional block diagram of an embodiment of orientation device 60. Orientation device 60 includes tilt detector 62, processor 80, memory 82, telemetry module 84, power source 86, and indicator 88. Processor 80 may include a microprocessor, a controller, a DSP, an ASIC, a FPGA, discrete logic circuitry, or the like. In some embodiments, processor 80 determines an orientation of aperture 64 of device 60 with the aid of instructions that are stored in memory 82.

For example, if tilt detector 62 is an accelerometer, the instructions may include algorithms for determining an offset between accelerometer outputs and a gravity vector in order to determine a relative orientation of device 60. As another example, the instructions stored in memory 82 may include algorithms that when implemented by processor 80, may be used to determine when the orientation of aperture 64 substantially matches the orientation of fill port opening 26A based on signals from tilt detector 62 of device 60 and tilt detector 58 of IMD 12. Processor 80 may receive signals from tilt detector 58 of IMD 12 via telemetry module 84. Memory 82 may include any volatile or non-volatile media, such as RAM, ROM, NVRAM, EEPROM, flash memory, and the like. Power source 86 may be, for example, a rechargeable or non-rechargeable battery.

Under the control of processor 80, telemetry module 84 (which may also be referred to as a "receiver") may communicate with IMD 12 via any suitable local wireless RF communication techniques. Telemetry module 84 may also communicate with other external devices with the aid of infrared communication techniques, such as communication according to the IRDA specification set or other standard or proprietary telemetry protocols. Orientation device 60 may also communicate with another programming or computing device via exchange of removable media, such as magnetic or optical disks, or memory cards or sticks. Further, device 60 may communicate with programmer 20 or another computing device via remote telemetry techniques known in the art, communicating via a LAN, WAN, PSTN, or cellular telephone network.

Figure 7:
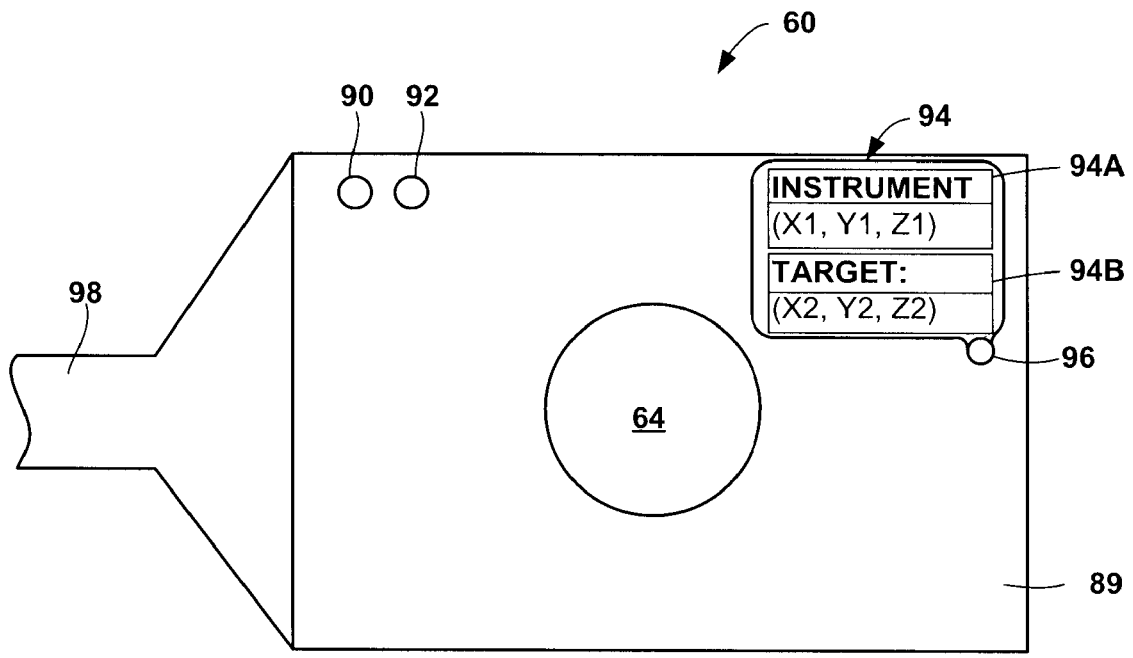
FIG. 7 is a schematic plan view of an embodiment of an orientation device.

Indicator 88 may be any suitable mechanism that provides information to a user. For example, as shown in FIG. 7, which is a schematic plan view of one embodiment of orientation device 60, indicator 88 may include lights 90, 92 and/or display 94. Lights 90, 92 each may each be, for example, a conventional light bulb, a light emitting diode (LED) or the like. Display 94 may be, for example, a LED display, light crystal display (LCD) or another type of monochrome or color display capable of presenting information to a user. In other embodiments, indicator 88 may include another suitable sensory feedback, such as other visual indication mechanisms, audio indicators, somatosensory indicators, and so forth. The sensory indicators may be used alone or in combination with at least one other type of sensor feedback. For example, indicator 88 may include both a light and a display that presents information to a user. As another example, indicator 88 may include a somatosensory alert generator (e.g., a pulse generator that causes at least a part of device 60 to vibrate in a pattern or randomly).

In the embodiment shown in FIG. 7, orientation device 60 further includes housing 89 that contains processor 80, tilt detector 62, memory 82, telemetry module 84, and power source 86, as well as input button 96 and handle 98. Housing 89 may, for example, substantially enclose processor 80, tilt detector 62, memory 82, telemetry module 84, and power source 86. Button 96 may have multiple functions. For example, when depressed for a relatively short duration (e.g., one second or less), button 96 may act as a reset button or to select different functions of orientation device 60, and when depressed for a longer duration (e.g., greater than one second), button 96 may be used to power device 60 on and off. Although a single button 96 is shown in FIG. 7, in other embodiments, orientation device 60 may include a plurality of input buttons, or display 94 may be a touch screen display that a user may interact with in order to provide input.

Housing 89 defines aperture 64. In order to align aperture 64 with fill port opening 26A of IMD 12 (FIGS. 3-4B), a user may change the orientation of orientation device 60, e.g., by grasping handle 98, until indicator 88 provides information that indicates aperture 64 is substantially aligned with fill port opening 26A of IMD 12. For example, in some embodiments, processor 80 of device 60 may receive electrical signals generated by tilt detector 62 and translate the signals into useful information, such as force vectors. In the embodiment shown in FIG. 7, display 94 includes a subdisplay 94A that provides output from tilt detector 62 in three directions (X1, Y1, Z1), which may be representative of x-axis, y-axis, and z-axis force vectors relative to a gravity vector. Processor 80 of device 60 may also receive electrical signals generated by tilt detector 58 of IMD 12, e.g., via wireless communication techniques, and translate the signals into substantially similar information. In the embodiment shown in FIG. 7, display 94 includes a subdisplay 94B that indicates the orientation of a "target," i.e., fill port opening 26A of IMD 12. However, the "target" may change, depending upon the portion of IMD 12 with which tilt detector 58 is associated. The orientation of the target is shown in terms of the force vectors in three directions (X2, Y2, Z2), which may be representative of x-axis, y-axis, and z-axis force vectors relative to a gravity vector.

Tilt detectors 58, 62 of IMD 12 and external orientation device 60 have a common reference point, such that the output from tilt detectors 58, 62 may be used to determine the relative orientation between fill port 26 of IMD 12 and aperture 64 of device 60. In embodiments in which tilt detectors 58, 62 are accelerometers, for example, tilt detectors 58, 62 share a common primary gravity vector. Thus, in order to substantially align an orientation of aperture 64 with an orientation of fill port opening 26A of IMD 12, the user may change the orientation of device 60 until the (X1, Y1, Z1) values substantially match the (X2, Y2, Z2) values of the target shown on display 94. For example, the user may change the orientation of device 60 until the (X1, Y1, Z1) values are within a certain range of the (X2, Y2, Z2) values of the target shown on display 94 or the same.

Instead of or in addition to output shown on display 94, the user may determine when aperture 64 of orientation device 60 is oriented to substantially match an orientation of fill port 26 based on visible feedback from lights 90, 92. For example, light 90 may be a red light that, when lit, indicates the device 60 and fill port opening 26A of IMD 12 are not oriented substantially similarly, and light 92 may be a green light that, when lit, indicates aperture 64 of device 60 and fill port 26 of IMD 12 are oriented substantially similarly, i.e., when the (X1, Y1, Z1) signals from tilt detector 62 substantially match the (X2, Y2, Z2) values of tilt detector 58 of IMD 12. Processor 80 of external orientation device 60 may receive signals from tilt detector 62 and tilt detector 58 of IMD 12 and determine when the signals indicate an orientation of device 60 substantially matches an orientation of fill port 26. Processor 80 may control indicator 88 to light red light 90 until the signals from tilt detectors 58, 62 indicate that an orientation of device 60 is within the desired orientation relative to fill port opening 26A, at which time processor 80 may control indicator 88 to light green light 92. Thus, a user may change an orientation of device 60 relative to epidermis surface 29 (FIG. 3) of patient 16 until green light 92 is activated. Assuming the location (as opposed to the orientation) of septum 40 of fill port assembly 25 (FIG. 3) is known, the user may then introduce needle 48 of external instrument 46 through aperture 64 in order to access septum 40 and fill port 26.

Other techniques for providing information to a user to indicate when device 60 (e.g., an orientation of aperture 64 of device 60) is in a desired orientation relative to an orientation of fill port 26 are contemplated. For example, in other embodiments, other information may be provided on display 94, such as, but not limited to, directions that direct a user to orient device 60 in order to substantially align orientation device 60 with fill port 26, where the directions may be in textual form, graphical form (e.g., an illustration of an orientation device 60 relative to epidermis 29) or a combination of text and graphics.

FIG. 8A is a flow diagram illustrating an embodiment of a technique for introducing needle 48 of external instrument 46 into fill port 26 of IMD 12 while IMD 12 is implanted within tissue 28 of patient 12. A user may locate fill port 26 (or septum 40) (100) using any suitable technique, such as those described in U.S. patent application Ser. No. 11/747,614, entitled, "SEPTUM PORT LOCATOR SYSTEM AND METHOD FOR AN IMPLANTABLE THERAPEUTIC SUBSTANCE DELIVERY DEVICE" and previously incorporated by reference. After locating fill port (100), the user may position aperture 64 of device 60 over epidermis 29 at the approximate determined fill port 26 location (102). For example, the user may mark epidermis 29 with a pen, marker or another device that generates a visible mark at the determined fill port 26 location, and center aperture 64 over the mark.

As previously described, in addition to knowing a location of fill port 26, it may be desirable to determine the orientation of fill port opening 26A in order to more accurately and precisely introduce needle 48 of external instrument 46 into opening 26A. Accordingly, the user may utilize orientation device 60 to position external instrument 46 such that an orientation of needle 48 substantially matches an orientation of fill port 26 within patient 12 (104). In particular, the user may orient device 60 based on information from tilt detector 58 of IMD 12 and tilt detector 62 of orientation device 60. The user may activate orientation device 60, e.g., by depressing button 96 (FIG. 7).

Tilt detector 58 is in a known orientation relative to fill port opening 26A. Thus, information from tilt detector 58 may be used to determine an orientation of fill port opening 26A. Similarly, tilt detector 62 is in a known orientation relative to aperture 64, such that information from tilt detector 58 may be used to determine an orientation of aperture 64. In addition, tilt detectors 58, 62 have a common reference, such that the relative position between fill port opening 26A and aperture 64 of device 60 may be determined based on information from tilt detectors 58, 62.

As previously described, processor 80 of orientation device 80 may provide information from tilt detectors 58, 62, e.g., by displaying vector values for instrument 80 and fill port 26 on display 94, as shown in FIG. 7, or via any other suitable information-providing technique. With the feedback technique shown in FIG. 7, the user may rotate orientation device 60 until the (X1, Y1, Z1) values output by tilt detector 62 of orientation device 60 substantially match the (X2, Y2, Z2) values output by tilt detector 58 of IMD 12. Upon receiving an indication from orientation device 60 that an orientation of aperture 64 substantially matches an orientation of fill port 26, the user may introduce needle 48 through aperture 64 and through epidermis 29 in order to access fill port 26 (106). The user may use orientation device 60 as a guide to determine the angle at which needle 48 should be percutaneously introduced through epidermis 29 in order to access fill port 26. For example, the user may place needle 48 substantially perpendicular to a major plane defined by the side of orientation device 60 defining aperture 64, as shown in FIG. 4B.

FIG. 8B is a flow diagram illustrating another embodiment of a technique for introducing needle 48 of external instrument 46 into fill port 26 of IMD 12 while IMD 12 is implanted within tissue 28 of patient 12. As with the technique shown in FIG. 8A, a user may locate fill port 26 (100) and position aperture 64 of orientation device 60 over epidermis 29 of patient 16 based on the determined location of port 26 (102). The user may then change the orientation of device (108), such as by rotating device in the x-axis, y-axis and/or z-axis directions (orthogonal x-z axes are shown in FIG. 3) while substantially maintaining aperture 64 over the determined location of port 26.

If indicator 88 of orientation device 60 indicates that the output of tilt detector 62 of orientation device 60 substantially matches the output of tilt detector 58 of IMD 12 (109), the user may introduce needle 48 through aperture 64 of orientation device 60 and through epidermis 29 in order to access fill port 26 (106). As previously indicated, indicator 88 may include alerts, such as a visible light, audible sound or tactile alert (e.g., device 60 or a portion of device 60 may vibrate), or a display 94 that a user may reference to determine when the output of tilt detector 62 of orientation device 60 substantially matches the output of tilt detector 58 of IMD 12, thereby indicating aperture 64 is substantially aligned with fill port opening 26A of IMD 12. Thus, according to the technique shown in FIG. 8B, the user may continue adjusting the orientation of device 60 relative to epidermis 29 of patient 16 until indicator 88 indicates that aperture 64 is substantially aligned with fill port opening 26A of IMD 12 (108, 109).

Although a separate medical instrument 46 and orientation device 60 are shown and described with respect to FIGS. 3-7, in other embodiments, a medical instrument and orientation device may be coupled together, such that the orientation device indicates the relative position of the medical instrument. FIG. 9 is a schematic illustration of medical instrument 110, which includes orientation device 112. Medical instrument 110 is similar to medical instrument 46, but is coupled to an orientation device 112. For example, medical instrument 110 includes needle 48 and fluid compartment 52. In some embodiments, needle 48 may be removably coupled to orientation device 112 to allow orientation device 112 to be used multiple times. Thus, in some cases, needle 48 may be disposable or sterilizable for use with more than one patient. In other embodiments, both needle 48 and orientation device 112 of medical instrument 110 may be disposable. A removable needle 48 may allow a clinician to access compartment 52 in order to, for example, fill compartment 52 with a therapeutic agent, change the agent retained within compartment, clean compartment 52, and so forth.

Orientation device 112 may include functional components similar to that of device 60 of FIGS. 6-7. However, orientation device 112 does not define an aperture configured to receive a medical instrument. Instead, orientation device 112 determines a relative orientation between fill port opening 26A of IMD 12 and instrument 110 based on the orientation of needle 48. For example, orientation device 112 may include a processor and tilt detector, similar to processor 80 and tilt detector 62, respectively, of orientation device 60. In the embodiment shown in FIG. 9, the processor and tilt detector of orientation device 112 are disposed within a common housing 113. The tilt detector of orientation device 112 may be in a known orientation relative to needle 48, such that signals generated by the tilt detector are indicative of the orientation of needle 48, rather than a separate orientation device.

In one embodiment, tilt detector 58 and the tilt detector of orientation device 112 may be positioned within IMD 12 and orientation device 112, respectively, such that the output from the tilt detectors substantially matches when a longitudinal axis of needle 48 is substantially perpendicular to fill port opening 26A, such that needle 48 may access opening 26A at any location along width $W_P$ of fill port opening 26A. A processor of orientation device 112 may analyze the offset between the outputs between tilt detector 58 of IMD 12 and a tilt detector associated with orientation device 112 to determine the relative orientation between needle 48 and fill port opening 26A. The relative orientation between needle 48 and fill port opening 26A generally refers to the position of needle 48 (e.g., a longitudinal axis of needle 48) relative to the position of fill port opening 26A (or the fill port opening 26A relative to needle 48). In addition, the relative orientation between needle 48 and fill port opening 26A may also indicate the direction in which fill port opening 26A may be facing within tissue 28 (i.e., a "tilt" of fill port opening 26A) relative to epidermis 29. Alternatively, tilt detector 58 and the tilt detector of orientation device 112 may be positioned within the respective devices such that the output from the tilt detectors matches when needle 48 has a different orientation relative to fill port opening 26A.

Just as with orientation device 60, orientation device 112 may provide information to a user, e.g., via display 114, which may be similar to display 94 of FIG. 7, to indicate when medical instrument 110 is oriented to substantially match an orientation of fill port 26 of IMD 12. The information may be the acceleration vectors generated by the respective tilt detectors of IMD 12 and instrument 110, an alert (e.g., a visible light, audible sound or tactile feedback) that indicates when instrument 110 is positioned to substantially match an orientation of fill port opening 26A of IMD 12 and/or textual or graphical directions for guiding the user to position instrument 110 to substantially match a determined orientation of fill port opening 26A.

Figure 10:
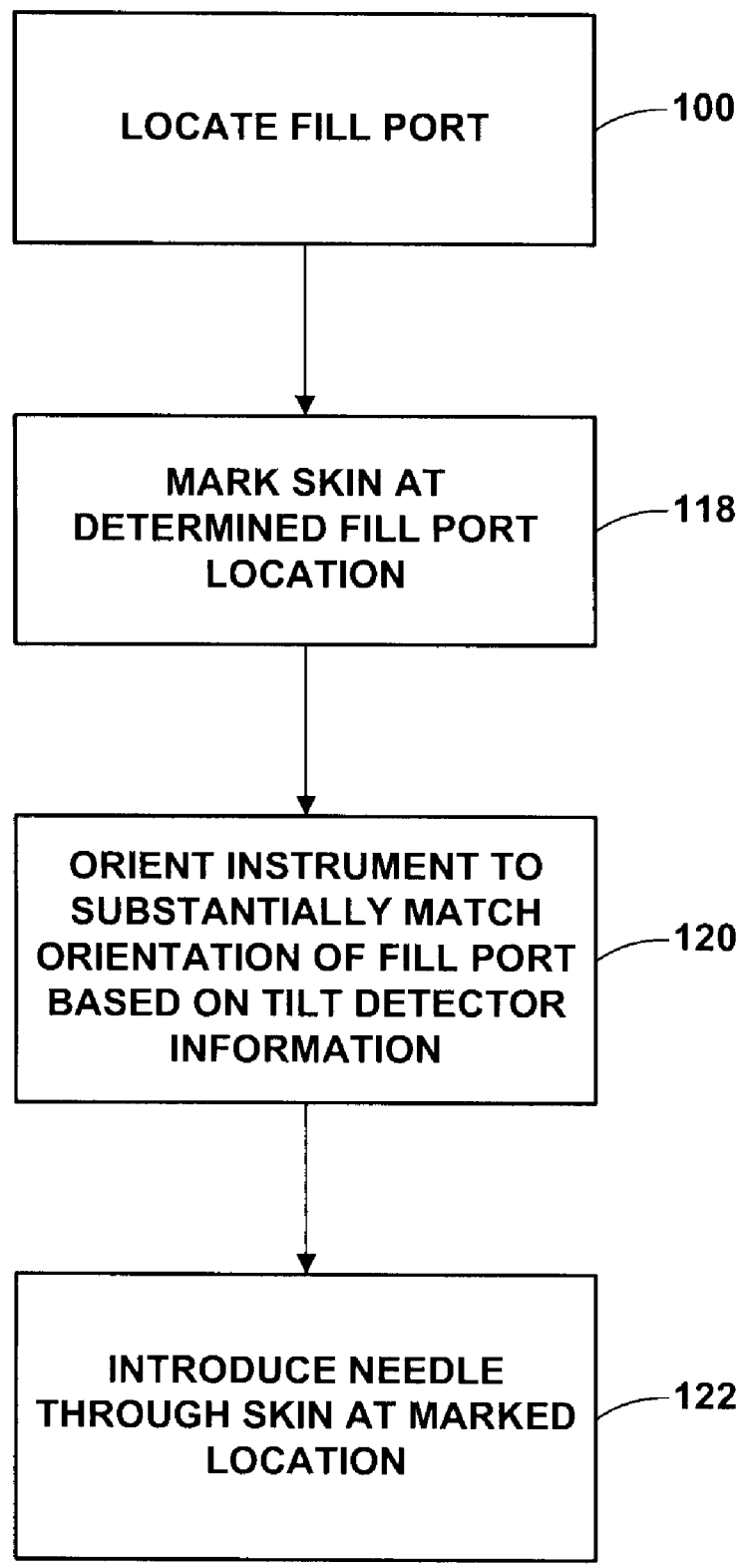
FIG. 10 is a flow diagram illustrating a technique for accessing an implanted medical device with the aid of the orientation system shown in FIG. 9.

FIG. 10 is a flow diagram illustrating an embodiment of a technique for accessing fill port 26 of IMD 12 with the aid of external instrument 110 of FIG. 9. A user may locate fill port 26 using any suitable technique (100). The user may mark the patient's epidermis 29 (FIG. 3) at the determined fill port 26 location, e.g., by placing a marker on the epidermis surface or by drawing a mark on epidermis 29 (118). In order to align an orientation of device 110 with an orientation of fill port opening 26A, the user may activate orientation device 112, e.g., by depressing button 116. However, in some embodiments, orientation device 112 may be automatically activated (i.e., powered up or woken up from a sleep state), e.g., via an accelerometer that detects when device 110 is moved.

Just as with orientation device 60 (FIGS. 3-7), orientation device 112 may receive signals from tilt detector 58 of IMD 12, which is in a known orientation relative to fill port opening 26A and provides information indicating an orientation of fill port 26. A processor within orientation device 112 may then provide information, e.g., by displaying vector values for instrument 110 and fill port 26 on display 114, as shown in FIG. 9, or via any other suitable feedback technique. With the feedback technique shown in FIG. 9, the user may rotate external instrument 110 until the (X1, Y1, Z1) values output by the tilt detector of orientation device 112 and shown on display 114 substantially match the (X2, Y2, Z2) values output by tilt detector 58 of IMD 12 and shown on display 114. Upon receiving an indication from orientation device 112 that needle 48 is oriented to substantially match an orientation of fill port 26 (120), the user may percutaneously introduce needle 48 through epidermis 29 at the marked location in order to access fill port 26 (122).

Figure 11:
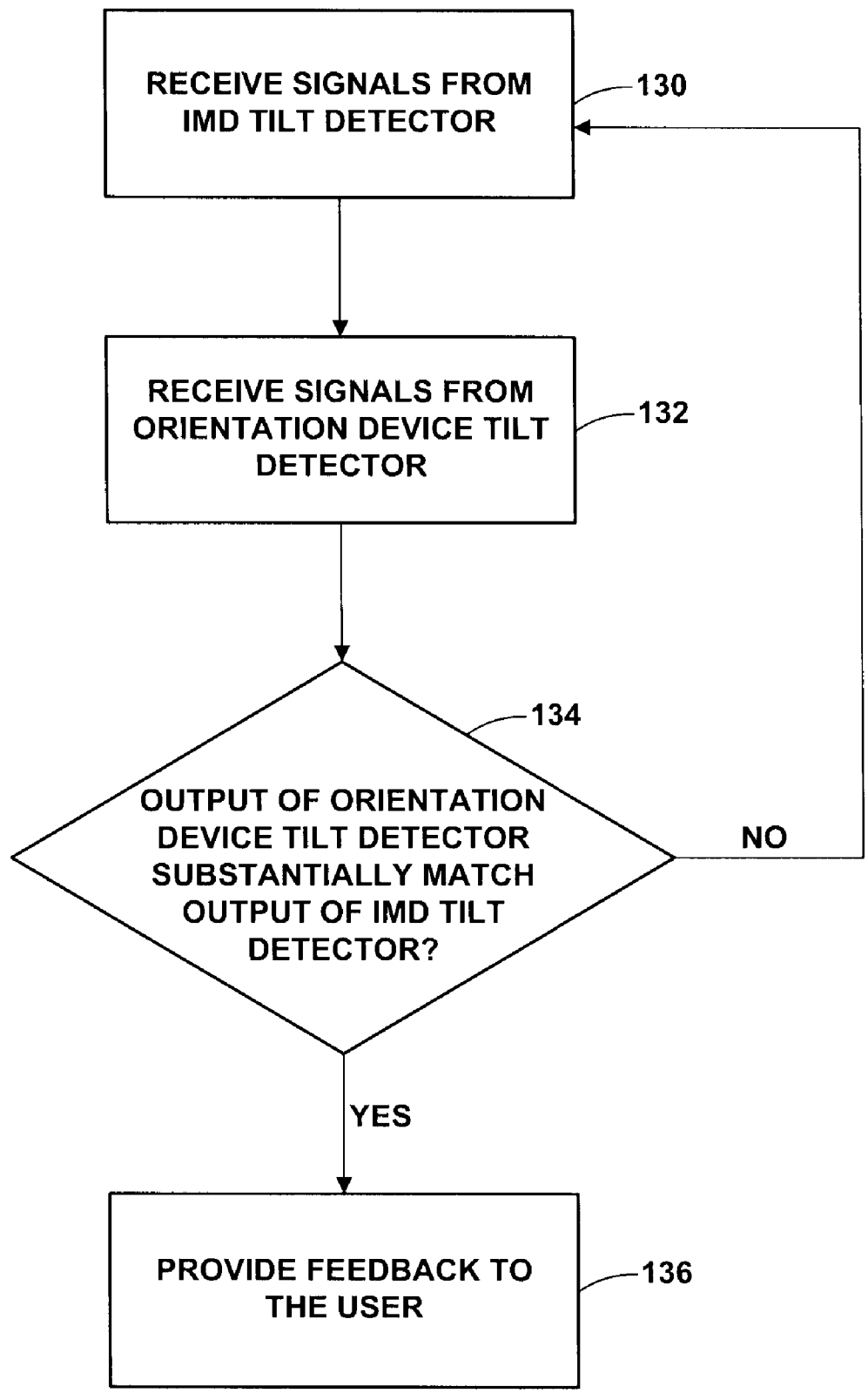
FIGS. 11-13 are flow diagrams illustrating different techniques that may be employed to orient a medical instrument relative to at least a portion of a medical device.
Figure 12:
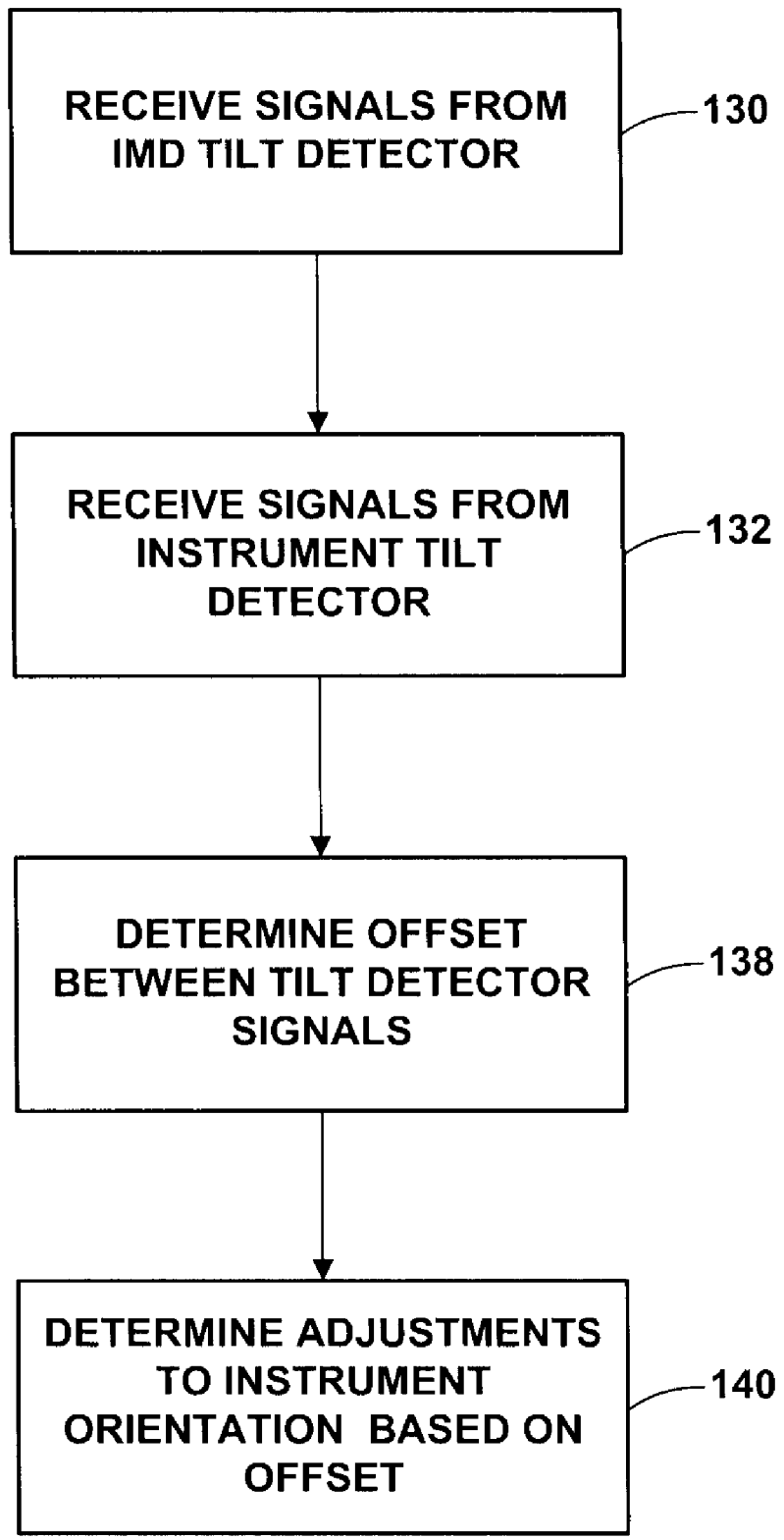
Figure 13:
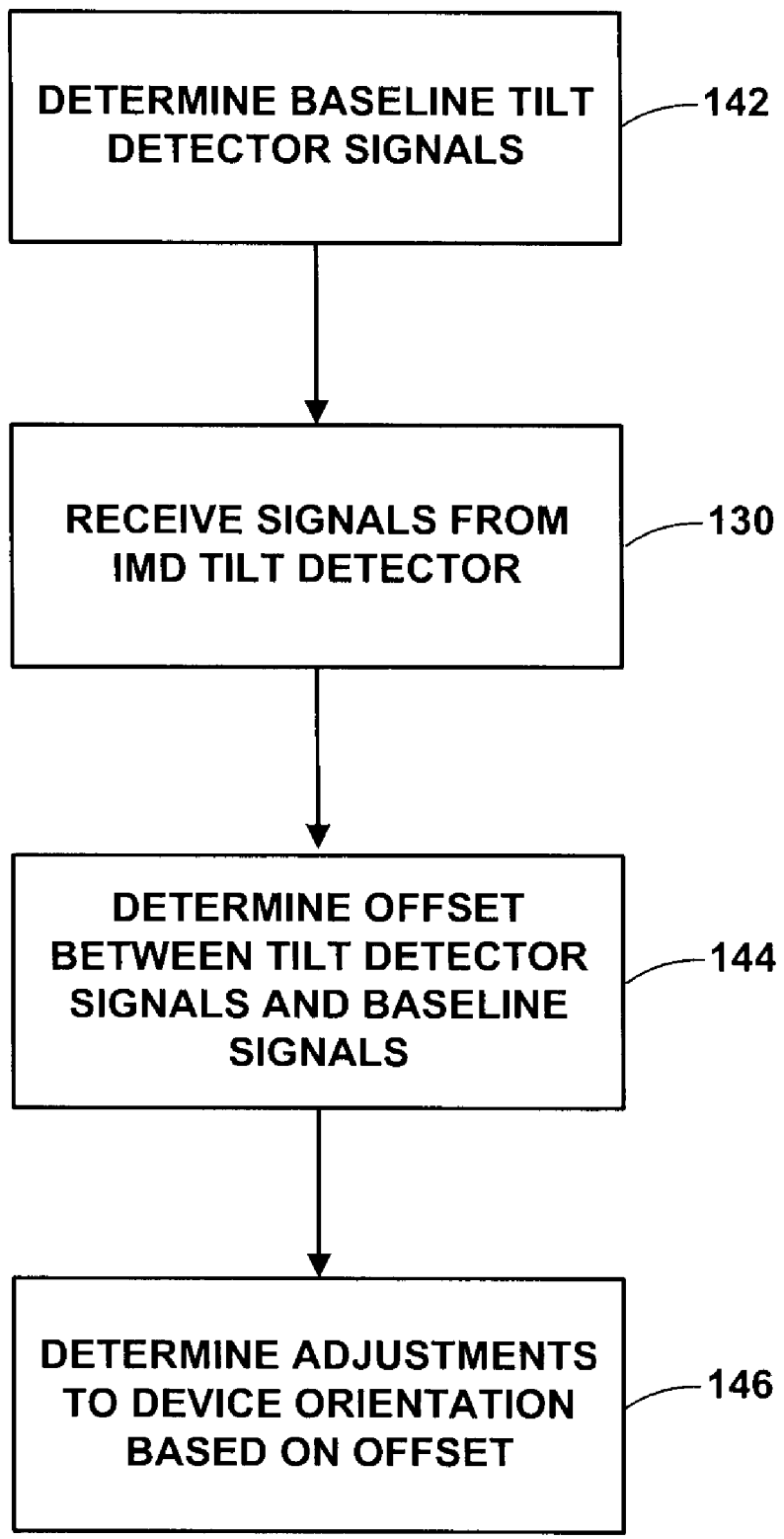

FIGS. 11-13 are flow diagrams illustrating different techniques that may be employed to determine when an orientation of an orientation device substantially matches an orientation of at least a portion of IMD 12, such as fill port opening 26A or to determine adjustments that may be made to an orientation of an external device in order to substantially match the orientation of the external device with the orientation of the portion of IMD 12. The techniques shown in FIGS. 11-13 may be employed, e.g., by a processor of an orientation device 60, 112, processor 70 of IMD 12, a processor of programmer 20 (FIG. 1) or a processor of another device. Although IMD 12, external instrument 46, and orientation device 60 (FIGS. 3-7) are referred to in the description of FIGS. 11-13, in other embodiments, the techniques shown in FIGS. 11-13 may be used to position external instrument 110 (FIG. 9) or another external instrument relative to a portion of any IMD 12 including a tilt detector.

FIG. 11 is a flow diagram illustrating an embodiment of a technique for determining when an orientation of orientation device 60 substantially matches an orientation of fill port opening 26A of IMD 12. Processor 80 of orientation device 60 may receive signals from tilt detector 58 of IMD 12 on a continuous basis or periodically (130). For example, telemetry module 74 of IMD 12 may transmit signals from tilt detector 58 to telemetry module 84 of orientation device 60 by RF communication techniques at a frequency of about 0.5 Hz to about 100 Hz. Alternatively, processor 80 may interrogate IMD 12 in order to receive signals from tilt detector 58. Processor 80 may also receive signals from tilt detector 62 of orientation device 60 (132). Tilt detector 62 may be electrically coupled to processor 80.

After receiving signals from tilt detector 58, 62, processor 80 may compare the signals to determine if the orientation of orientation device 60 substantially matches an orientation of fill port opening 26A, e.g., by determining whether the outputs of tilt detectors 58, 62 substantially match (134). If the outputs do not substantially match, i.e., do not match or are not within a certain range, processor 80 may continue monitoring the signals from tilt detectors 58, 62 (130, 132). If the outputs indicate the orientation of orientation device 60 substantially matches an orientation of fill port opening 26A, processor 80 may control indicator 88 to provide information to a user (136).

FIG. 12 is a flow diagram illustrating an embodiment of a technique for determining an orientation of orientation device 60 based on information from tilt detector associated with IMD 12. Processor 80 of orientation device 60 may receive signals from tilt detectors 58, 62 (130, 132). Processor 80 may determine the offset between the signals (138). For example, in embodiments in which tilt detectors 58, 62 are three-axis accelerometers, tilt detector 62 may output signals (X1, Y1, Z1) that indicate the acceleration vectors in the x-axis, y-axis, and z-axis directions relative to a primary acceleration vector and tilt detector 58 may output signals (X2, Y2, Z2) that indicate the acceleration vectors in the x-axis, y-axis, and z-axis directions relative to the same primary acceleration vector as tilt detector 62. The offset between the outputs of tilt detectors 58, 62 may be, for example, (X1-X2, Y1-Y2, Z1-Z2).

Based on the determined offset between the signals, which may indicate the relative differences in orientation between aperture 64 of orientation device 60 and fill port opening 26A of IMD 12, processor 80 may determine adjustments to the orientation of device 60 (140). As previously described, in embodiments in which tilt detectors 58, 62 are three-axis accelerometers, processor 80 may correlate a certain change in acceleration vectors with a certain magnitude of movement. For example, a certain change in the acceleration vector in the x-axis direction, $\Delta X$, may be associated with a one centimeter movement in the positive x-axis direction. After determining the offset in acceleration vectors output by tilt detectors 58, 62, processor 80 may determine the direction and magnitudes of movement necessary to align the orientation of aperture 64 with fill port opening 26A.

FIG. 13 is a flow diagram illustrating an embodiment of a technique for determining an orientation of fill port opening 26A based on information from tilt detector 58 of IMD 12, which is associated with fill port opening 26A. Processor 80 may determine baseline tilt detector signals (142). As previously described, the baseline tilt detector signals may be the output of tilt detector 58 at a baseline orientation of fill port opening 26A, e.g., at the time IMD 12 was implanted within patient 12 and prior to any change in angulation of IMD 12 within patient 16. The signals may be stored within memory 82 of orientation device 60, memory 72 of IMD 12 or a memory of another device.

After receiving signals from tilt detector 58 (130), processor 80 may analyze the offset between the output of tilt detectors 58 of IMD 12 and the baseline tilt detector signals to determine the tilt of fill port opening 26A relative to the baseline position (144). Processor 80 may then determine the extent to which fill port opening 26A is tilted within patient 16 based on the offset and determine the direction and magnitudes of movement necessary to orient device 60 such that the orientation of aperture 64 substantially matches an orientation of fill port opening 26A (146). Processor 80 may correlate a certain change in acceleration vectors (or magnitude of magnetic fields) with a certain magnitude of movement, and use these correlated values to guide a user to orient device 60 such that aperture 64 is substantially aligned with fill port opening 26A. In some embodiments, the instructions may be presented on display 94 of device 60.

Figure 14:
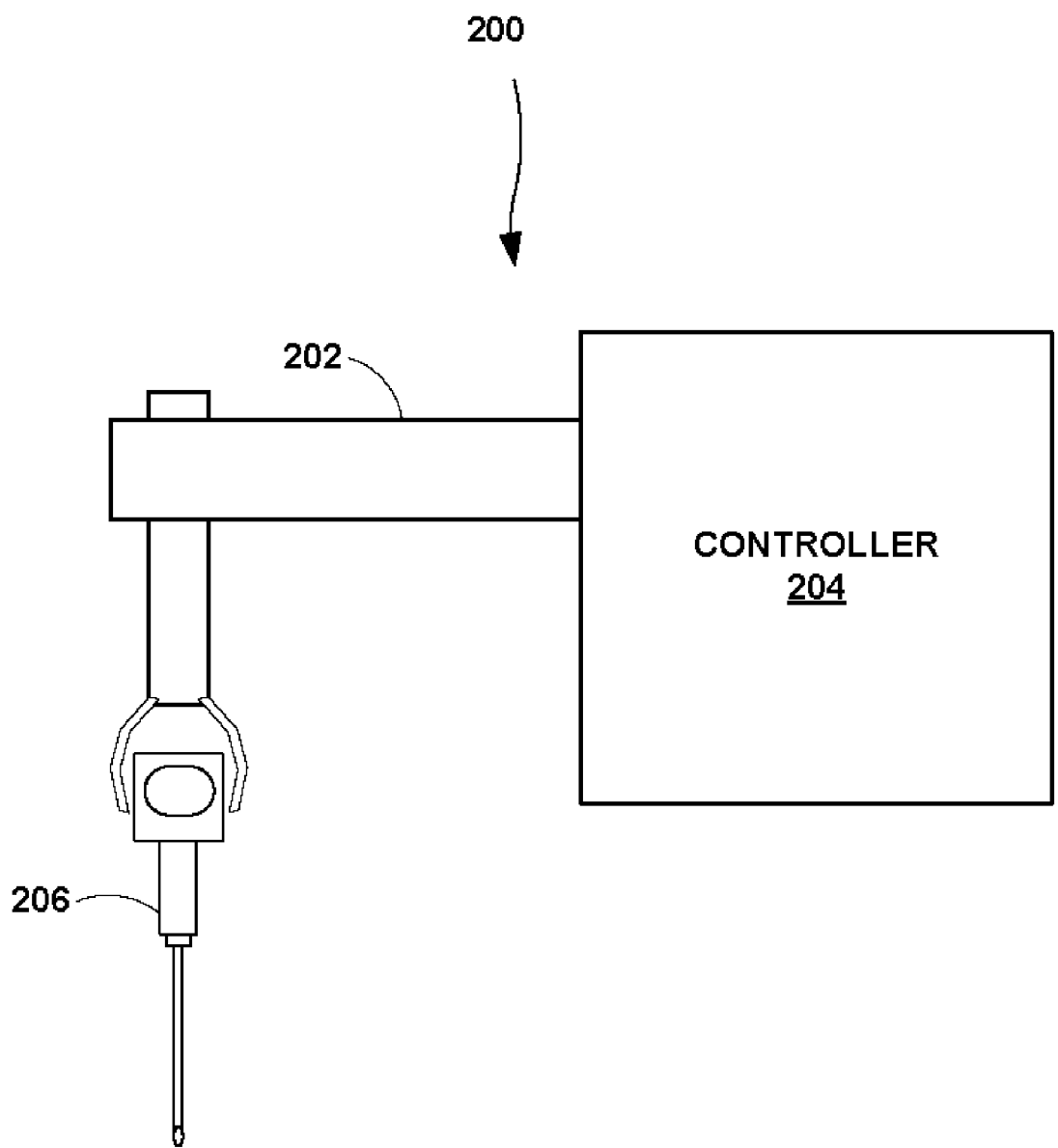
FIG. 14 is a conceptual diagram illustrating a positioning device for positioning a medical instrument relative to at least a portion of a medical device.

Various embodiments of the invention have been described. These and other embodiments are within the scope of the following claims. For example, while techniques for manually positioning an external instrument based on tilt detectors associated with the external instrument and an IMD are described, in other embodiments, a positioning device may automatically or semi-automatically position the external instrument under the control of a processor or another controller. In one embodiment, such as the example illustrated in FIG. 14, a positioning device 200 may include a mechanical arm 202 coupled to a controller 204. The mechanical arm 202 may grasp the external instrument 206, and the controller 204 may position the external instrument 206 (e.g., via computer-numerical control techniques) based on signals from the tilt detector associated with the IMD and the signals from the tilt detector associated with the external instrument 206.

In addition, although techniques for determining when an orientation device or a medical instrument are in a desired orientation relative to at least a portion of IMD 12 are primarily described with reference to techniques employed by a processor of the orientation device, in other embodiments, a processor of another device may make such a determination. For example, processor 70 of IMD 12, a processor of programmer 20 or another computing device may determine when the orientation device or medical instrument are in a desired orientation relative to at least a portion of IMD 12, and provide information to a user relating to the same (e.g., an alert to indicate a successful positioning of the device or instructions on how to orient the device to achieve the desired orientation).

The systems and methods described herein are not limited to orienting an external instrument relative to fill port 26 of IMD 12. Embodiments of a tilt alignment system described herein may include a tilt detector in a known orientation with another portion of an IMD.

The invention claimed is:
1. A system comprising:
an implantable medical device comprising a first tilt detector in a known orientation relative to at least a portion of the implantable medical device;
an orientation device comprising a second tilt detector; and an indicator that provides information to a user based on signals from the first and second tilt detectors, wherein the information is indicative of a relative orientation between the orientation device and the portion of the implantable medical device,
wherein the first tilt detector comprises a first accelerometer, and
wherein the second tilt detector comprises a second accelerometer.

2. The system of claim 1, wherein the signals comprise a first signal from the first tilt detector and a second signal from the second tilt detector, and the information indicates whether the first signal substantially matches the second signal.

3. The system of claim 1, further comprising a processor that determines the relative orientation between the orientation device and the portion of the implantable medical device based on the signals from the first and second tilt detectors.

4. The system of claim 3, wherein the signals comprise a first signal from the first tilt detector and a second signal from the second tilt detector, and the processor determines an offset between the first signal and the second signal to determine the relative orientation between the orientation device and the portion of the implantable medical device.

5. The system of claim 3, wherein the signals comprise a first signal from the first tilt detector, and the processor determines an offset between the first signal and a baseline signal, and the information comprises instructions to guide a user to position the orientation device relative to the portion of the implantable medical device based on the offset.

6. The system of claim 1, wherein the indicator comprises at least one of a display, a light or a somatosensory alert generator.

7. The system of claim 1, further comprising an external medical instrument coupled to the orientation device.

8. The system of claim 7, wherein the implantable medical device comprises a reservoir and a fill port in fluid communication with the reservoir, and the external instrument comprises a needle configured to be introduced into the fill port.

9. The system of claim 1, further comprising a processor that controls a positioning device that automatically positions an external medical instrument relative to the implantable medical device based on the signals from the first and second tilt detectors.

10. The system of claim 1, further comprising a processor that generates instructions to guide a user to position the orientation device relative to the portion of the implantable medical device based on the signals from the first and second tilt detectors, wherein the information comprises the instructions.

11. An orientation device comprising:
a first tilt detector comprising a first accelerometer;
a receiver that receives signals from a second tilt detector comprising a second accelerometer associated with an implantable medical device; and
an indicator that provides information to a user based on signals from the first and second tilt detectors, wherein the information is indicative of a relative orientation between the orientation device and the implantable medical device.

12. The device of claim 11, further comprising a housing, wherein the first tilt detector and a processor are disposed in the housing, the device further comprising a needle and fluid compartment coupled to the housing.

13. A method comprising:
receiving a first signal from a first tilt detector comprising a first accelerometer, the first tilt detector being associated with an implantable medical device;
receiving a second signal from a second tilt detector comprising a second accelerometer, the second tilt detector being associated with an orientation device; and
providing information to a user indicative of a relative orientation between at least a portion of the implantable medical device and the orientation device based on the first and second signals.

14. The method of claim 13, wherein providing information to the user comprises indicating whether the first signal substantially matches the second signal.

15. The method of claim 13, wherein providing information to the user comprises displaying information indicative of the first signal and the second signal on a display.

16. The method of claim 13, further comprising determining an offset between the first signal and the second signal, wherein providing information to the user comprises providing information indicative of the offset.

17. The method of claim 16, further comprising determining an adjustment to a position of the orientation device relative to the implantable medical device based on the offset.

18. The method of claim 16, further comprising automatically positioning an external medical instrument relative to the implantable medical device based on the offset.

19. A method comprising:
placing an external device in a first position relative to an implantable medical device, wherein the implantable medical device comprises a first tilt detector comprising a first accelerometer and the external device is associated with a second tilt detector comprising a second accelerometer;
receiving information indicative of a relative orientation between the implantable medical device and the external device, wherein the information is based on a first signal from the first tilt detector and a second signal from the second tilt detector; and
adjusting the external device to place the external device in a second position relative to the implantable medical device based on the first and second signals.

20. A system comprising:
means for receiving a first signal from a first tilt detector comprising a first accelerometer associated with an implantable medical device;
means for receiving a second signal from a second tilt detector comprising a second accelerometer associated with an orientation device; and
means for providing information to a user indicative of a relative orientation between at least a portion of the implantable medical device and the orientation device.

* * * * *